(12) United States Patent
Staehle et al.

(10) Patent No.: US 8,912,202 B2
(45) Date of Patent: Dec. 16, 2014

(54) N-(BENZIMIMDAZOL-2-YL)-CYCLOPROPANE CARBOXAMIDES AS LYSOPHOSPHATIDIC ACID ANTAGONISTS

(75) Inventors: Wolfgang Staehle, Ingelheim (DE); Melanie Schultz, Darmstadt (DE); Kai Schiemann, Seeheim-Jugenheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/237,446

(22) PCT Filed: Jul. 7, 2012

(86) PCT No.: PCT/EP2012/002874
§ 371 (c)(1),
(2), (4) Date: Mar. 18, 2014

(87) PCT Pub. No.: WO2013/020622
PCT Pub. Date: Feb. 14, 2013

(65) Prior Publication Data
US 2014/0228378 A1    Aug. 14, 2014

(30) Foreign Application Priority Data

Aug. 8, 2011   (EP) .................................. 11006501

(51) Int. Cl.
| | | |
|---|---|---|
| *C07D 513/02* | (2006.01) | |
| *A61K 31/52* | (2006.01) | |
| *C07D 473/00* | (2006.01) | |
| *C07D 235/30* | (2006.01) | |
| *A61K 31/416* | (2006.01) | |
| *A61K 31/4184* | (2006.01) | |
| *A61K 31/437* | (2006.01) | |
| *A61K 31/454* | (2006.01) | |
| *C07D 231/56* | (2006.01) | |
| *C07D 235/32* | (2006.01) | |
| *C07D 401/12* | (2006.01) | |
| *C07D 403/12* | (2006.01) | |
| *C07D 417/04* | (2006.01) | |

(52) U.S. Cl.
CPC ............ *C07D 473/00* (2013.01); *C07D 235/30* (2013.01); *A61K 31/416* (2013.01); *A61K 31/4184* (2013.01); *A61K 31/437* (2013.01); *A61K 31/454* (2013.01); *A61K 31/52* (2013.01); *C07D 231/56* (2013.01); *C07D 235/32* (2013.01); *C07D 401/12* (2013.01); *C07D 403/12* (2013.01); *C07D 417/04* (2013.01)
USPC ........................................ 514/263.4; 546/118

(58) Field of Classification Search
None
See application file for complete search history.

(56) References Cited

FOREIGN PATENT DOCUMENTS

| EP | 2481752 A1 | 8/2012 |
|---|---|---|
| WO | 2011041462 A2 | 4/2011 |

OTHER PUBLICATIONS

International Preliminary Report on Patentability, Jan. 28, 2014.

*Primary Examiner* — Heidi Reese

(57) ABSTRACT

The invention provides novel substituted cyclopropane carboxamide compounds according to Formula (I), their manufacture and use for the treatment of proliferative or inflammatory diseases, such as cancer, fibrosis or arthritis.

19 Claims, No Drawings

N-(BENZIMIMDAZOL-2-YL)-CYCLOPROPANE CARBOXAMIDES AS LYSOPHOSPHATIDIC ACID ANTAGONISTS

FIELD OF THE INVENTION

The invention relates to a series of novel substituted cyclopropane carboxamide compounds that are useful in the treatment of proliferative of inflammatory diseases, such as cancer, in mammals. Also encompassed by the present invention is the use of such compounds in the treatment of hyperproliferative diseases in mammals, especially humans, and pharmaceutical compositions containing such compounds.

RELATED APPLICATIONS

This application is a U.S. national stage application of PCT international application PCT/EP2012/002874, filed on Jul. 7, 2012, which claims the benefit of European patent application number 11006501.8, filed on Aug. 8, 2011. The entire contents of the aforementioned applications are hereby incorporated by reference.

SUMMARY OF THE RELATED ART

Lysophospholipids are membrane-derived bioactive lipid mediators. Lysophospholipids affect fundamental cellular functions that include proliferation, differentiation, survival, migration, adhesion, invasion, and morphogenesis. These functions influence many biological processes that include, but are not limited to, neurogenesis, angiogenesis, wound healing, fibrosis, immunity, and carcinogenesis.

Lysophosphatidic acid (LPA) is a lysophospholipid that has been shown to act through sets of specific G protein-coupled receptors (GPCRs) in an autocrine and paracrine fashion. LPA binding to its cognate GPCRs (LPA$_1$, LPA$_2$, LPA$_3$, LPA$_4$, LPA$_5$, LPA$_6$) activates intracellular signaling pathways to produce a variety of biological responses. Antagonists of the LPA receptors find use in the treatment of diseases, disorders or conditions in which LPA plays a role, especially in hyperproliferative diseases, such as cancer.

In ascites and plasma of ovarian cancer patients increased LPA levels were detected. LPA has been shown to promote tumor cell proliferation, survival, migration and invasion. Increased levels of LPA, altered receptor expression and altered responses to LPA may contribute to the initiation, progression or outcome of ovarian cancer. LPA is potentially also involved many other types of cancer, such as prostate, breast, melanoma, head and neck, bowel and thyroid cancers. Therefore, a LPA receptor antagonist (preferably sub-type selective) should be able to decrease these effects, most likely resulting in a positive outcome in cancer progression.

LPA primarily exert its biological effects via G protein-coupled receptors, such as EDG-2/LPA1, EDG-4/LPA2, EDG-7/LPA3, GPR23/LPA4, GPR93/LPA5, p2y5/LPA6. Especially EDG-4/LPA2 and EDG-7/LPA3 are consistently up-regulated in malignant ovarian epithelial cells contributing to the aberrant response of ovarian cancer cells to LPA. These receptors kick off signalling through the $G_i$, the $G_{q,11}$, or the $G_{12,13}$ pathways in the cell. Alteration of the signalling through these pathways is common to all drugs targeting GPCRs, which account for more than half of the marketed drugs today in various indications.

High levels of LPA are generated during blood coagulation due to the release of phospholipase PLA1 and sPLA2 from platelets that convert phosphatidic acid to LPA. LPA is considered to be one of the most potent growth factors in serum used for the growth of cells in vitro.

DESCRIPTION OF THE INVENTION

It is the object of the present invention to provide novel LPA receptor antagonists useful in the treatment of hyperproliferative diseases, especially those related to the hyperactivity of LPA, such as cancer, fibrosis or arthritis, in mammals, with superior pharmacological properties both with respect to their activities as well as their solubility, metabolic clearance and bioavailability characteristics.

As a result, this invention provides novel substituted cyclopropane carboxamide compounds or their stereoisomers or tautomers, or pharmaceutically acceptable salts, that are LPA antagonists and useful as medicaments, especially in the treatment of the above mentioned diseases.

The compounds are defined by Formula (I):

wherein:

$R^{1'}$, $R^{1''}$, $R^{4'}$, $R^{4''}$ are independently H, Hal, OH, CN, NO$_2$, NH$_2$, A, NH(LA), N(LA)$_2$, COOH, $R^2$, $R^3$ are independently H, LA or Hal, $R^5$, $R^6$ are independently H or LA, X is CH or N, wherein 0, 1 or 2 X are N, and the remaining X are CH, A is a unbranched or branched alkyl based substituent having up to 15 carbon atoms, wherein one, two or three CH$_2$ groups may be replaced by O, S, NH, N(LA), CONH, NHCO, SO$_2$, COO or cyc, and 1-7H atoms may be replaced by Hal, and one CH$_3$ group may be replaced by cyc, LA is unbranched or branched alkyl having 1, 2, 3 or 4 carbon atoms, cyc is a mononuclear, aliphatic or aromatic, 4, 5 or 6 membered homo or heterocycle having 1 to 3 N-, O- and/or S atoms, and Hal is F, Cl, Br or I.

In general, all residues which occur more than once may be identical or different, i.e. are independent of one another. Above and below, the residues and parameters have the meanings indicated for the Formula (I), unless expressly indicated otherwise. Accordingly, the invention relates, in particular, to the compounds of the Formula (I) in which at least one of the said residues has one of the preferred meanings indicated below.

Hal denotes fluorine, chlorine, bromine or iodine, in particular fluorine or chlorine.

"A" denotes, for example, methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, or 1-ethylpropyl.

"A" further denotes alkyl as defined above, in which one CH$_2$ group may be replaced by O or S atoms and/or an —NH—, —CO—, —NHCOO—, —NHCONH—, —CONH—, —NHCO—, —CH=CH—, —N=CH— or —CH=N— group, and in which 1-5H atoms may be replaced by Hal, and in which one CH group may be replaced by N, and in which one CH$_3$ group may be replaced by CN, such as, for example, trifluoromethyl, pentafluoroethyl, 1,1-difluoromethyl, 1,1,1-trifluoroethyl, methoxy, ethoxy, n-propoxy, isopropoxy, n-butoxy, isobutoxy, sec-butoxy or tert-butoxy, N,N'-dimethylaminoalkyl, 2-aminoethyl, 3-aminopropyl, 4-aminobutyl, 5-aminopentyl, 3-aminomethylcyclobutyl or cyanoalkyl.

"A" further denotes alkyl as defined above, in which one CH$_2$ group may be replaced by cyc, such as 2-pyrrolidin-1-yl-ethoxy, 3-(benzyl-oxy-carbonyl)pyrrolidin-1-yl-methyl amino, 1-benzyl-piperidin-4-yl-methyl amino.

"LA" denotes unbranched or branched, linear alkyl having 1, 2, 3 or 4 C atoms, wherein 1, 2 or 3H atoms may be replaced by Hal, e.g. methyl, ethyl, trifluoromethyl, difluoromethyl, 1,1,1-trifluoroethyl, propyl, isopropyl, butyl, isobutyl, sec-butyl or tert-butyl.

"Cyc" denotes, for example, cyclobutyl, cyclopentyl, cyclohexyl, azetidine-1-, 2- or 3-yl, oxazolidine-2-, 3-, 4- or 5-yl, isoxazolidine-2-, 3-, 4- or 5-yl, 2,3-dihydro-2-, -3-, -4- or -5-furyl, 2,5-dihydro-2-, -3-, -4- or -5-furyl, tetrahydro-2- or -3-furyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3-, 1-, 5- or 6-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, phenyl, 2- or 3-furyl, 2- or 3-thienyl, 1-, 2- or 3-pyrrolyl, 1-, 2- or 3-pyrrolidinyl, 1-, 2,4- or 5-imidazolyl, 1-, 3-, 4- or 5-pyrazolyl, 2-, 3- or 4-pyridyl, 2-, 4-, 5- or 6-pyrimidinyl, 2-, 3-, 5-, or 6-pyrazin-1- or 4-yl, 1,2,3-triazol-1-, -4- or -5-yl, 1,2,4-triazol-1-, -3- or 5-yl, 1- or 5-tetrazolyl.

The following compounds are known from chemical libraries and are, therefore, as far as composition of matter protection is concerned, excluded from claims 15-19 of this patent application:

2-Phenyl-cyclopropanecarboxylic acid (6-methanesulfonyl-benzothiazol-2-yl)-amide, Phenyl-cyclopropanecarboxylic acid (1H-benzoimidazol-2-yl)-amide, N-[1-[2-(diethylamino)ethyl]-1H-benzimidazol-2-yl]-2-phenyl-cyclopropane carboxamide, N-(1-methyl-1H-benzimidazol-2-yl)-2-phenyl-cyclopropane carboxamide, 2-phenyl-N-(1-propyl-1H-benzimidazol-2-yl-cyclopropane carboxamide, N-(1-ethyl-1H-benzimidazol-2-yl)-2-phenyl-cyclopropane carboxamide, 2-(4-chlorophenyl)-N-(1-methyl-1H-benzimidazol-2-yl)-cyclopropane carboxamide, or N-1H-benzimidazol-2-yl-2-phenyl-cyclopropane carboxamide.

In a preferred embodiment conforming to Formula (I'), the two substituents at the cyclopropyl ring which are not R$^2$, R$^3$, are trans oriented:

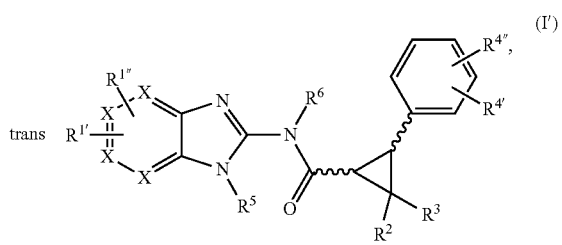

wherein all residues have the meaning indicated for Formula (I).

More preferred groups of compounds of Formula (I') conform to Formulae (II'), (III'), (IV'), (V') or (VI'):

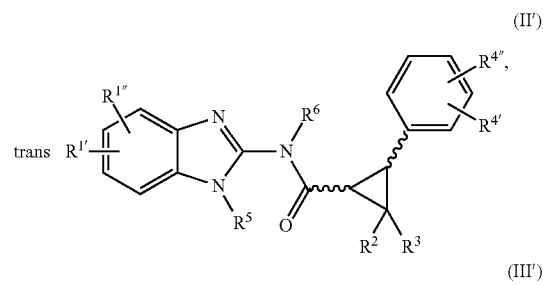

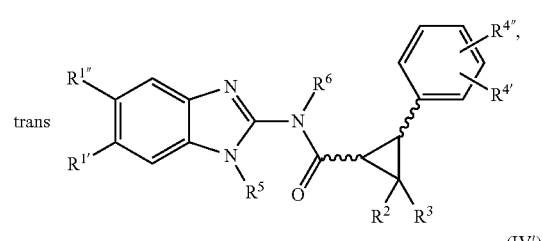

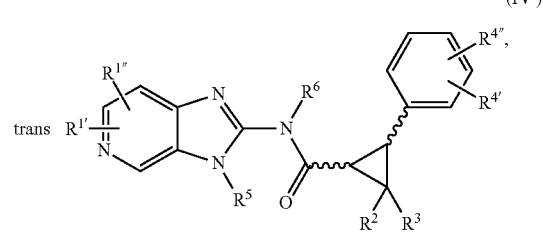

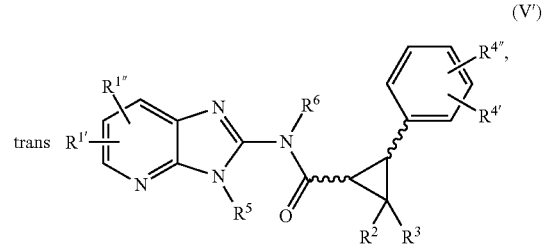

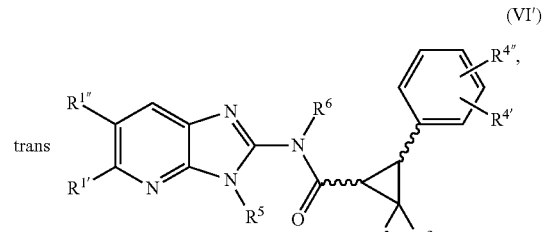

in which all residues have the meaning indicated for Formula (I).

In another preferred embodiment conforming to Formula (I"), the stereochemistry at the cyclopropyl ring is as follows:

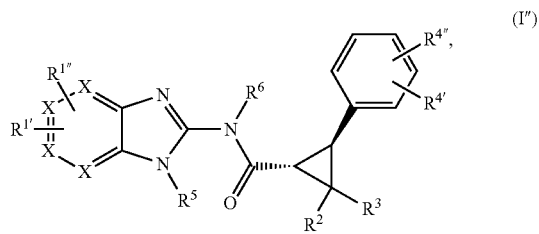

More preferred groups of compounds of Formula (I") conform to Formulae (II"), (III"), (IV"), (V") or (VI"):

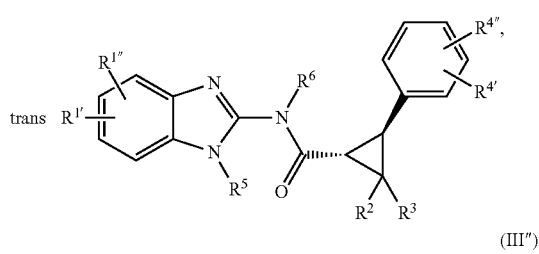

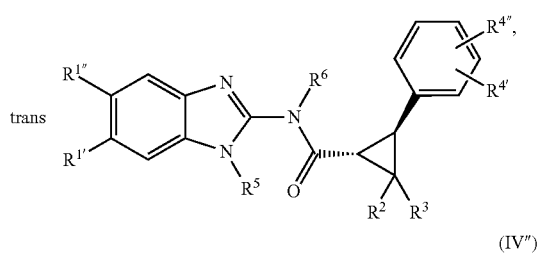

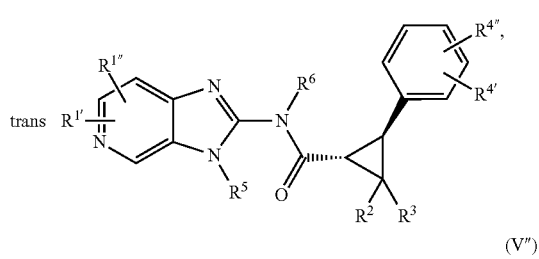

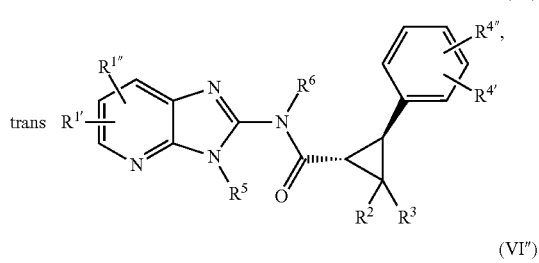

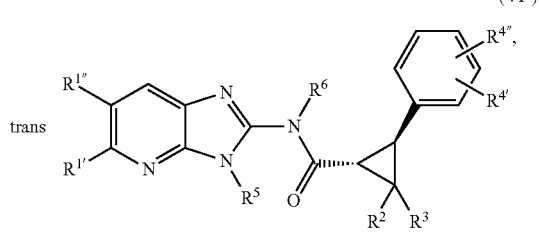

in which all residues have the meaning indicated for Formula (I).

Further preferred are compounds of Subformulae 1 to 12 of Formulae (I), (I'), (I"), (II'), (II"), (III'), (III"), (IV'), (IV"), (V'), (V"), (VI') or (VI"), wherein
in Subformula 1
$R^{1'}$, $R^{1''}$ are independently H, F, Cl, Br, CN, $NO_2$, methyl or ethyl,
in Subformula 2
$R^{1'}$ is H,
$R^{1''}$ is F, Cl, Br, CN, $NO_2$, methyl or ethyl,
in Subformula 3
$R^{1''}$ is H, and
$R^{1'}$ is F, Cl, Br, CN, $NO_2$, methyl or ethyl,
in Subformula 4
$R^{4'}$, $R^{4''}$ are independently H, F, Cl or Br,
in Subformula 5
$R^2$, $R^3$ are independently H or F,
in Subformula 6
$R^5$, $R^6$ are H,
in Subformula 7
$R^{1'}$ is H,
$R^{1''}$ is Cl or Br,
in Subformula 8
$R^{1'}$ is CN,
$R^{1''}$ is H,
in Subformula 9
$R^{4'}$, $R^{4''}$ are H,
in Subformula 10
$R^{4'}$ is meta-Fluoro,
$R^{4''}$ is H,
in Subformula 11
$R^{1'}$, $R^{1''}$ are H,
in Subformula 12
$R^2$, $R^3$ are H,
and the remaining residues have the meaning as indicated for Formula (I).

Especially preferred are those compounds of Formulae (Formulae (I), (I'), (I"), (II'), (II"), (III'), (III"), (IV'), (IV"), (V'), (V"), (VI') or (VI"), wherein $R^5$ is H.

The compounds of the Formula (I) may have one or more centres of chirality. They may accordingly occur in various enantiomeric forms and be in racemic or optically active form. The invention, therefore, also relates to the optically active forms, enantiomers, racemates, diastereomers, collectively: stereoisomers, of these compounds.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

An elegant method for the resolution of racemates containing ester groups (for example acetyl esters) is the use of enzymes, in particular esterases.

The compounds of the present invention can be in the form of a prodrug compound. "Prodrug compound" means a derivative that is converted into a biologically active compound according to the present invention under physiological conditions in the living body, e.g., by oxidation, reduction, hydrolysis or the like, each of which is carried out enzymatically, or without enzyme involvement. Examples of prodrugs are compounds, wherein the amino group in a compound of the present invention is acylated, alkylated or phosphorylated, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated, or wherein a sulfhydryl group forms a disulfide bridge with a carrier molecule, e.g. a peptide, that delivers the drug selectively to a target and/or to the cytosol of a cell. These compounds can be produced from compounds of the present invention according to well-known methods. Other examples of prodrugs are compounds, wherein the carboxylate in a compound of the present invention is for example converted into an alkyl-, aryl-, choline-, amino, acyloxymethylester, linolenoyl-ester.

Where tautomerism, e.g., keto-enol tautomerism, of compounds of the present invention or their prodrugs may occur, the individual forms, e.g., the keto or the enol form, are claimed separately and together as mixtures in any ratio. The same applies for stereoisomers, e.g., enantiomers, cis/trans isomers, conformers and the like.

If desired, isomers can be separated by methods well known in the art, e.g. by liquid chromatography. The same applies for enantiomers, e.g., by using chiral stationary phases. Additionally, enantiomers may be isolated by converting them into diastereomers, i.e., coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials The compounds of the present invention can be in the form of a pharmaceutically acceptable salt, a pharmaceutically acceptable solvate, or a pharmaceutically acceptable solvate of a pharmaceutically acceptable salt.

The term "pharmaceutically acceptable salts" refers to salts prepared from pharmaceutically acceptable bases or acids, including inorganic bases or acids and organic bases or acids. In cases where the compounds of the present invention contain one or more acidic or basic groups, the invention also comprises their corresponding pharmaceutically acceptable salts. Thus, the compounds of the present invention which contain acidic groups can be present in salt form, and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the present invention which contain one or more basic groups, i.e. groups which can be protonated, can be present in salt form, and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

The term "pharmaceutically acceptable solvates" means addition forms with pharmaceutically acceptable solvents that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, e.g. a mono- or dihydrate. If the solvent is alcohol, the solvate formed is an alcoholate, e.g., a methanolate or ethanolate. If the solvent is an ether, the solvate formed is an etherate, e.g., diethyl etherate.

Therefore, the following items are also in accordance with the invention:
 a) all stereoisomers or tautomers of the compounds, including mixtures thereof in all ratios,
 b) prodrugs of the compounds, or stereoisomers or tautomers of these prodrugs,
 c) pharmaceutically acceptable salts of the compounds and of the items mentioned under (a) and (b),
 d) pharmaceutically acceptable solvates of the compounds and of the items mentioned under (a), (b) and (c).

It should be understood that all references to compounds above and below are meant to include these items, in particular pharmaceutically acceptable solvates of the compounds, or pharmaceutically acceptable solvates of their pharmaceutically acceptable salts.

Furthermore, the present invention relates to pharmaceutical compositions comprising a compound of the present invention, or its stereoisomers or tautomers, or pharmaceutically acceptable salts of each of the foregoing, including mixtures thereof in all ratios, as active ingredient, together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as active ingredients, such as one or more additional compounds of the present invention, or other LPA antagonists.

The pharmaceutical compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In one embodiment, said compounds and pharmaceutical composition are for the treatment of cancer such as brain, lung, colon, epidermoid, squamous cell, bladder, gastric, pancreatic, breast, head, neck, renal, kidney, liver, ovarian, prostate, colorectal, uterine, rectal, oesophageal, testicular, gynecological, thyroid cancer, melanoma, hematologic malignancies such as acute myelogenous leukemia, multiple myeloma, chronic myelogenous leukemia, myeloid cell leukemia, glioma, Kaposi's sarcoma, or any other type of solid or liquid tumors. Preferably, the cancer to be treated is chosen from glioblastoma, melanoma, ovarian, prostate, breast, head and neck, bowel and thyroid cancer.

The invention also relates to the use of a compound according to the invention for the preparation of a medicament for the treatment of proliferative or inflammatory diseases related to the hyperactivity of LPA as well as diseases modulated by LPA in mammals, or disorders mediated by aberrant proliferation, such as cancer.

This invention also relates to a compound or pharmaceutical composition for inhibiting abnormal cell growth in a mammal which comprises an amount of a compound of the present invention, in combination with an amount of another anti-cancer therapeutic, wherein the amounts of the compound, and of the other anti-cancer therapeutic are together effective in inhibiting abnormal cell growth. Many anti-cancer therapeutics are presently known in the art. In one embodiment, the anti-cancer therapeutic is a chemotherapeutic selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, integrin antagonists, such as cilengitide, and anti-androgens. In another embodiment the anti-cancer therapeutic is an antibody selected from the group consisting of bevacizumab, CD40-specific antibodies, chTNT-1/B, denosumab, zanolimumab, IGF1R-specific antibodies, lintuzumab, edrecolomab, WX G250, rituximab, ticilimumab, trastuzumab and cetuximab. In yet another embodiment the anti-cancer therapeutic is an inhibitor of a protein kinase, such as Akt, Axl, Aurora A, Aurora B, dyrk2, epha2, fgfr3, igf1r, IKK2, JNK3, Vegfr1, Vegfr2, Vegfr3 (also known as Flt-4), KDR, MEK, MET, Plk1, RSK1, Src, TrkA, Zap70, cKit, bRaf, EGFR, Jak2, PI3K, NPM-Alk, c-Abl, BTK, FAK, PDGFR, TAK1, LimK, Flt-3, PDK1 and Erk.

This invention further relates to a method for inhibiting abnormal cell growth in a mammal or treating a hyperproliferative disorder that comprises administering to the mammal an amount of a compound of the present invention or pharmaceutical composition, in combination with radiation therapy, wherein the amounts of the compound or pharmaceutical composition, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of a compound of the invention, or pharmaceutical composition, in this combination therapy can be determined as described herein. It is believed that the compounds of the present invention can render abnormal cells more sensitive to treatment with radiation for purposes of killing and/or inhibiting the growth of such cells.

Accordingly, this invention further relates to a method for sensitizing abnormal cells in a mammal to treatment with radiation which comprises administering to the mammal an amount of a compound of the present invention or pharmaceutical composition, which amount is effective in sensitizing abnormal cells to treatment with radiation. The amount of the compound in this method can be determined according to the means for ascertaining effective amounts of such compounds described herein.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like. In the case of oral liquid preparations, any of the usual pharmaceutical media may be employed, such as, for example, suspensions, elixirs and solutions; or carriers such as starches, sugars, microcrystalline cellulose, diluents, granulating agents, lubricants, binders, disintegrating agents and the like. In the case of oral solid preparations the composition may take forms such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing cancer, inflammation or other proliferative diseases for which compounds of the present invention are indicated, generally satisfactory results are obtained when the compounds of the present invention are administered at a daily dosage of from about 0.01 milligram to about 100 milligram per kilogram of body weight, preferably given as a single daily dose. For most large mammals, the total daily dosage is from about 0.1 milligrams to about 1000 milligrams, preferably from about 0.2 milligram to about 50 milligrams. In the case of a 70 kg adult human, the total daily dose will generally be from about 0.2 milligrams to about 200 milligrams. This dosage regimen may be adjusted to provide the optimal therapeutic response.

The invention also relates to a set (kit) consisting of separate packs of
a) an effective amount of a compound according to the invention or its stereoisomers or tautomers, or pharmaceutically acceptable salts of each of the foregoing, including mixtures thereof in all ratios, and
b) an effective amount of a further medicament active ingredient.

The set comprises suitable containers, such as boxes, individual bottles, bags or ampoules.

By way of example, the set may comprise separate ampoules, each containing an effective amount of a compound according to the invention, and an effective amount of a further medicament active ingredient in dissolved or lyophilised form.

EXPERIMENTAL SECTION

Some abbreviations that may appear in this application are as follows:

ABBREVIATIONS

| Designation | |
|---|---|
| ACN | acetonitrile |
| ATP | Adenosine triphosphate |
| b | Broad peak |
| d | Doublet |
| DMSO | dimethylsulfoxide |
| DTT | dithiothreitol |
| EDTA | Ethylenediaminetetraacetic acid |
| equiv. | equivalents |
| Et | ethyl |

-continued

| Designation | |
|---|---|
| h | hour |
| HEPES | 4-(2-hydroxyethyl)-1-piperazineethanesulfonic acid |
| HPLC | High Pressure Liquid Chromatography |
| LC/MS | Liquid Chromatography coupled to Mass Spectrometry |
| m | multiplet |
| M | Molecular ion |
| m/z | Mass-to-charge ratio |
| Me | methyl |
| min | minute |
| MS | Mass spectrometry |
| N | Normal (unit of concentration) |
| NMR | Nuclear Magnetic Resonance |
| PG | Protecting group |
| psi | Pounds per square inch |
| q | Quartette (or quartet) |
| Rf | Retention factor |
| RT | Room temperature |
| Rt. | Retention time |
| s | Singlet |
| Tert | Tertiary |
| THF | Tetrahydrofuran |
| UV | ultraviolet |
| VIS | visible |
| DMEM | Dulbecco's Modified Eagle's Medium |
| FCS | Fetal Calf Serum |
| PBS | Phosphate Buffered Saline |
| HBBS | Hank's Balanced Salt Solution |
| BSA | Bovine Serum Albumin |

The compounds of the present invention can be prepared according to the procedures of the following Schemes and Examples, using appropriate materials and are further exemplified by the following specific examples.

Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The instant compounds are generally isolated in the form of their pharmaceutically acceptable salts, such as those described above. The amine-free bases corresponding to the isolated salts can be generated by neutralization with a suitable base, such as aqueous sodium hydrogencarbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization.

The invention will be illustrated, but not limited, by reference to the specific embodiments described in the following examples. Unless otherwise indicated in the schemes, the variables have the same meaning as described above.

Unless otherwise specified, all starting materials are obtained from commercial suppliers and used without further purifications. Unless otherwise specified, all temperatures are expressed in ° C. and all reactions are conducted at room temperature. Compounds were purified by either silica chromatography or preparative HPLC.

The present invention relates also to a process for the manufacture of compounds of Formula (I), wherein a compound of Formula (VIII)

13

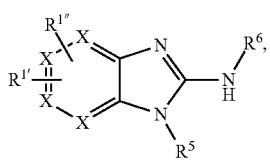

(VIII)

is reacted with a compound of Formula (VII)

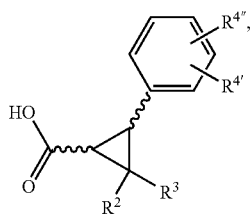

(VII)

to yield a compound of Formula (I).

EXAMPLES

Analytical LC

Gradient: 4.2 min/Flow: 2 ml/min 99:01-0:100 Water+ 0.1%(Vol.)TFA; Acetonitril+0.1%(Vol.)TFA; 0.0 to 0.2 min: 99:01; 0.2 to 3.8 min: 99:01→0:100; 3.8 to 4.2 min: 0:100; Column: Chromolith Performance RP18e; 100 mm long, 3 mm diameter; Wavelength: 220 nm.

Preparative HPLC

Preparative HPLC was performed using either a Merck Chromolith Prep, 100-25, RP-18e, Cat. No. 1.25252.0001 column. The column was used at a flow rate of 30 mL/min on a Merck-Knauer Prep HPLC K-1800 System equipped with an Merck-Knauer UV detector K-2600. The mobile phase was drawn from two solvent reservoirs containing (A) water and (B) HPLC-grade acetonitrile. A typical preparative run used a linear gradient (e.g., 0-100% solvent B over 20 min).

The working examples presented below are intended to illustrate particular embodiments of the invention, and are not intended to limit the scope of the specification or the claims in any way.

14

Chemical Synthesis

In this section experimental details are provided for a number of Example compounds according to Formula (I), and synthesis intermediates thereof.

1. 2-(3-Fluoro-phenyl)-cyclopropanecarboxylic acid (6-cyano-1H-benzoimidazol-2-yl)-amide (3)

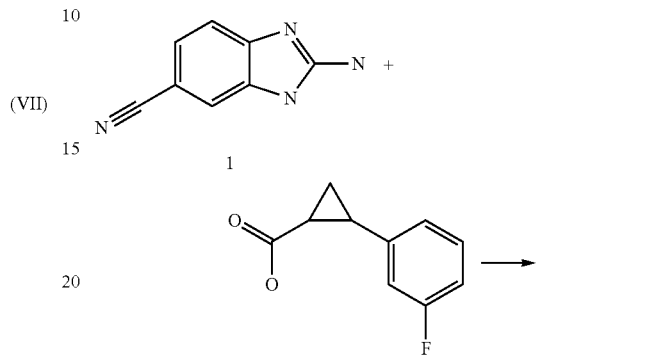

2-(3-Fluoro-phenyl)-cyclopropanecarboxylic acid 2 (90 mg, 0.50 mmol) was dissolved in 10 ml DMF. 115 mg (0.6 mmol) 1-Ethyl-3-(3-dimethylaminopropyl) carbodiimide hydrochloride (EDC) and 81 mg (0.6 mmol) 1-Hydroxybenzotriazole (HOBT) were added. The mixture was stirred for 30 min at room temperature (RT). Then 97 mg (0.5 mmol) 2-Amino-3H-benzoimidazole-5-carbonitril hydrochloride 1 were added to the mixture, which was stirred for 16 h at RT. After removing the solvent in vacuo, 20 ml water were added, whereupon the mixture was extracted 3 times with 50 ml acetic acid ethylester. The organic phases were combined, dried with sodium sulfate, and evaporated to dryness. The residue was separated via preparative HPLC. The resulting clean fractions were concentrated and lyophilized. 91 mg (57%) of a colorless, amorphous solid 3 were obtained.

2. 2,2-Difluoro-3-phenyl-cyclopropane carboxylic acid-(5-chloro-1H-benzoimidazol-2-yl)-amide 9

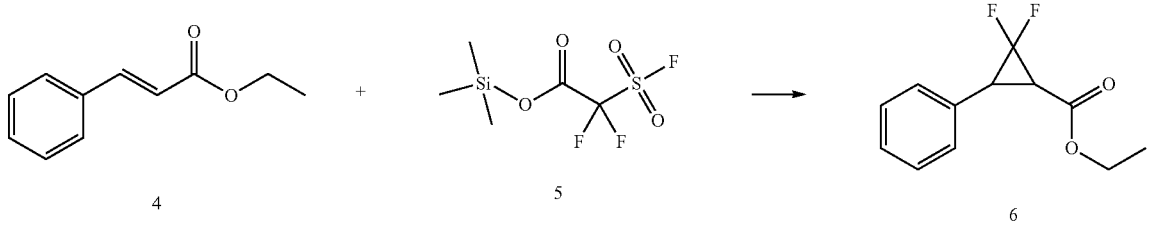

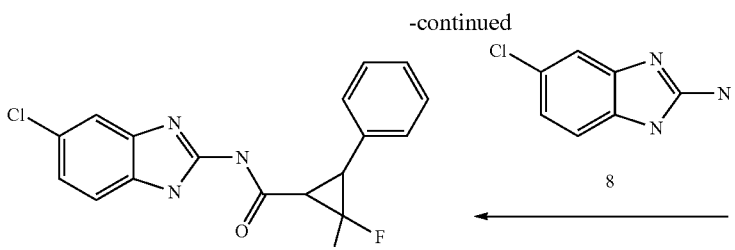
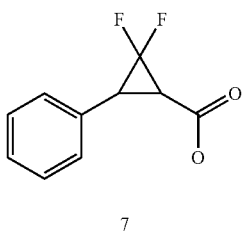

a. In a 25 ml two-necked flask 10 mg NaF (0.23 mmol) and 2.0 g (11.3 mmol) ethyl cinnamate were mixed with 1.2 ml Toluene (11.3 mmol). The reaction vessel was inertized with nitrogen and stirred at 105° C. for 16 hours. Then trimethylsilyl-2,2-difluoro-2-(fluorsulfonyl)acetate (TFDA 5 (5.0 ml, 24.1 mmol) was added continuously with a syringe pump over 5 h (development of gas). After all TFDA was added, the mixture was stirred for another hour at 105° C., whereupon the mixture was allowed to cool down to RT while stirring. Then 50 ml water were added, and the mixture extracted 3 times with 100 ml diethyl ether. The organic phases were combined, dried with sodium sulfate, and evaporated to dryness. 2.48 g of a yellow oil were obtained, containing 65% of 6.

b. 1.00 g (65% ig) (2.87 mmol) of 6 was dissolved in 10 ml THF, and refluxed with 1.3 ml of aqueous NaOH (32%) for 16 h. Then the solvent was evaporated in vacuo. 20 ml water was added, and the mixture extracted 3 times with 50 ml acetic ester. The organic phases were combined, dried with sodium sulfate, and evaporated to dryness. The crude product contained the desired product 7 and cinnamic acid in ratio of 1:1, and was not purified any further. Yield: 1.10 g (2.77 mmol, 96%) of a yellow crystallisate.

c. 295 mg (1.49 mmol) of 7 were reacted with 6-Chloro-1H-benzoimidazol-2-ylamine (250 mg, 1.49 mmol) 8 as described in example 1 above to yield 9. 57 mg (22%) of a colorless lyophilisate were obtained.

3. 2,2-dimethyl-3-phenyl-cyclopropane carboxylic acid-(1H-benzoimidazol-2-yl)-amide 15

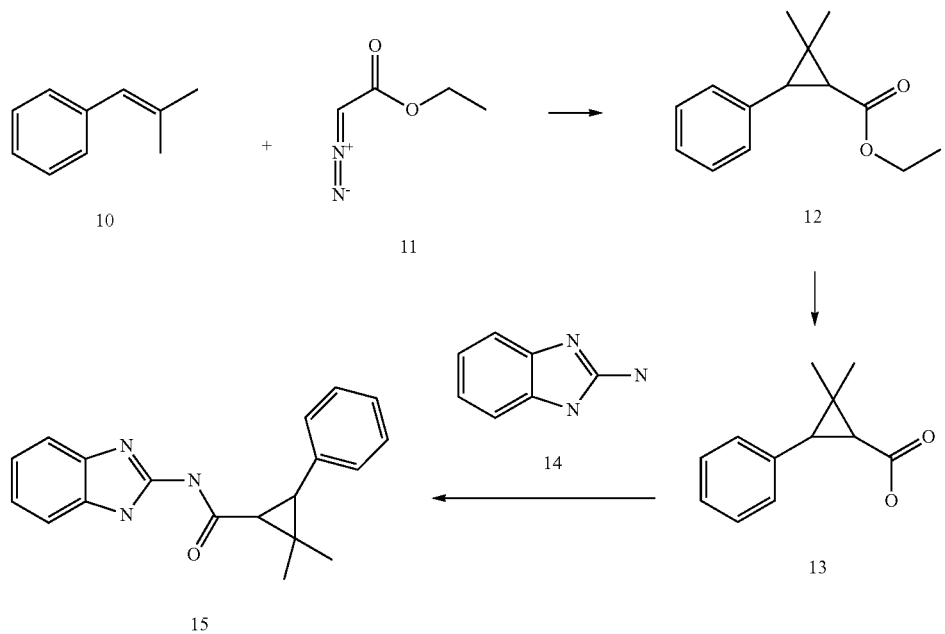

a. In a 100 ml round-bottom flask 800 mg (6.06 mmol) (2-Methyl-propenyl)-benzene 10 and 90 mg (0.56 mmol) anhydrous copper sulfate were heated to 110° C. Then a mixture of 3.2 g (24.2 mmol) 10 and 5 g (37.2 mmol) diazo-acetic acid ethyl ester 11 was added dropwise within 3 h at 110° C. while stirring. The mixture was allowed to cool down to RT while stirring. Insoluble solids were filtered off, and washed with DCM. The filtrate was added to 15 g silica gel, and purified by chromatography over 150 g silica gel with heptan/diethyl ether, yielding 1.55 g (20%) of a colorless liquid 12.

b. 1.55 g (7.1 mmol) of 12 were dissolved in 20 ml THF, and mixed with 5 ml aqueous NaOH (32%). The mixture was refluxed for 16 h. The THF was evaporated in vacuo, the aqueous solution acidified with 2N HCl, and extracted 2 times with 50 ml DCM. The organic phase was extracted with 2N NaOH, the aqueous phase acidified again with HCl, and again extracted with 2×50 ml DCM. The organic phase was washed with 20 ml saturated NaCl solution, dried with sodium sulfate, filtrated and evaporated. The free acid 13 was obtained as a clear oil which crystallized later. Yield: 1.21 g, (90%).

c. 230 mg (1.17 mmol) of 13 were reacted with 1H-benzoimidazol-2-ylamin 14 (160 mg, 1.17 mmol) as described in example 1 to yield 15. 18 mg (5%) of a colorless lyophilizated were obtained.

Biological Activity

1. Biochemical Enzyme Assay for LPA Activity

The assay detects intra cellular calcium which is generated by cells upon activation of the LPA2 receptor by its ligand LPA. This transient calcium mobilization can be monitored using a commercial calcium detection kit (e.g. from Molecular Devices). The main component of such a kit is a dye, which becomes fluorescent when calcium is present—a transient fluorescence signal after addition of a ligand to a test well are the result. Readers like the FLIPR (Molecular Devices) can be used to monitor such transient "Ca-flux" signals.

The signals are calculated according to peak maximum minus base line.

Compounds which are antagonists of LPA lead to a decreased mobilisation of intracellular calcium and thus to a lower signal. The assay is performed in microplates (384 wells per plate).

Reagents

| Cell culture | |
| --- | --- |
| cell line | U2OS, recombinant expressing LPA2R |
| McCoy's Medium | Invitrogen # 26600-021 |
| DMEM | Gibco #41965 |
| Penicillin/Streptomycin | Gibco #15140 |
| FCS | PAA # A15-043 |
| Geniticin | Invitrogen #10131-027 |
| PBS | Gibco |
| HEPES | Gibco #15630-056 |
| HyQ-Tase | HyClone #SV30030.01 |
| Assay | |
| 10 x HBSS | Gibco #14065 |
| 1M HEPES | Merck #1.10110 |
| NaCl | Merck #1.06404 |
| KCl | Merck #1.04936 |
| $MgSO_4 \times 7H_2O$ | Merck #1.05886 |
| $CaCl_2 \times 2H_2O$ | Merck #1.02382 |
| D(+)-Glucose × $1H_2O$ | Merck #1.04074 |
| BSA, fatty acid free | Roche #10 77 58 35 001 |
| ligand (LPA), 1-Oleoyl-2-Hydroxy-sn-Glycero-3-Phosphate, Avanti #857130P | |
| probenecid, water soluble | Invitrogen #P36400 |
| detection solution (calcium dye) | Bulk Kit (Molecular Devices #R8141) |
| micro plate 384 blck, cl. bottom | Falcon # 353692 |

Cell Cultivation/Propagation

| medium | McCoy's Medium, 10% FCS, 1 mg/ml Geniticin |
| --- | --- |
| culture conditions | 37° C., 5% $CO_2$ in T75 flasks |
| harvesting | washing with PBS |
| | detaching with 1 mL HyQ-Tase per flask |
| | incubation 5 min |
| | addition of 10 mL medium |
| | centrifugation |
| | re-suspension with 10 mL culture medium |

LPA2R-Calciumflux Assay Protocol

The assay is run according to the following procedure:

50 uL seed cells (10000 cells/well in DMEM buffer)
  Incubate 24 h at 37° C., 10% $CO_2$
  aspirate medium
50 uL add calcium dye 1×HBSS/HEPES buffer
  incubate 1 h at 37° C. ("loading")
  equilibrate 10 min at RT
5 uL add compounds in HEPES buffer
  shake 10 sec. at 1000 rpm
  incubate 15 min at RT
20 uL add LPA (in the FLIPR Tetra) in Krebs-buffer/BSA & measurement The cells are seeded in DMEM buffer (DMEM, 10% FCS, 10 mM HEPES, 1% Pen/Strep).

Dye loading is done in HBSS/HEPES buffer (100 mL 10×HBSS+20 mL 1M HEPES+880 mL water, pH 7.4)

The LPA is added in Krebs/BSA buffer (120 mM NaCl, 5 mM KCl, 0.62 mM $MgSO_4$, 1.8 mM $CaCl_2$, 10 mM HEPES, 6 mM D(+)-Glucose, 0.2% BSA, pH 7.4).

The compounds are pre-diluted in HEPES buffer (20 mM, pH 7.4), whereby the final DMSO content in the assay is kept at 1%. The compounds are pre-diluted in order to generate dose response series on the microplates. The dose response series consist of 10 concentrations for each compound from 30 uM final to 1 nM final. From all compound wells the resulting signals are referred to control wells (located on each plate besides the compound wells) in terms of % activity.

$$\% \text{ activity} = \frac{(readout_{compoupd} - readout_{blank})}{(readout_{full} - readout_{blank})} * 100$$

From these % activity values—along with the corresponding compound concentrations—IC50 values are fitted for each compound using standard fitting programs such as Graphpad Prism. Here the method "log(inhibitor) vs. response—Variable slope" is used.

Reader Settings (FLIPR Tetra)
ExcWLength: 470__495
Em.Wlength: 515__575
Gain: 50
Exp. Time: 0.4
Exc.Intensity: 80
READ with TF
First read interval: 1.00 s
Number of first reads: 240
Reads before dispense: 10
Second read interval: 1.00 s
Number of second reads: 0
Save Images: No To assess the inhibitory potential of the compounds on LPA2R, $IC_{50}$-values were determined, as shown in Table 1 below, whereby the following classification is used:

$IC_{50}$<10 nM "++++"
10 nM≤$IC_{50}$<100 nM "+++"
100 nM≤$IC_{50}$<1 μM "++"
1 μM≤$IC_{50}$≤10 μM "+"
$IC_{50}$>10 μM no symbol All compounds shown in Table 1 have the trans configuration at the cyclopropyl ring. For those compounds where the term "enantiomer" is used in connection with the structure, the $IC_{50}$ value was determined for one or both enantiomers possible for the trans configuration. In all other cases the $IC_{50}$ value was determined for the racemate of the two trans enantiomers.

| | IC₅₀ (LPA2R) | Chemical Name | NMR |
|---|---|---|---|
| 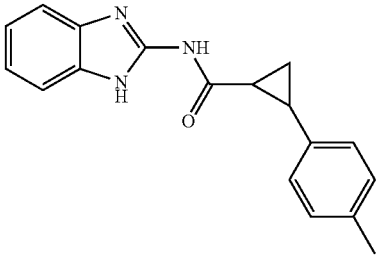 [SMILES: Cc1ccc(C2CC2C(=O)Nc2nc3ccccc3[nH]2)cc1] | + | 2-p-Tolyl-cyclopropane-carboxylic acid (1H-benzoimidazol-2-yl)-amide | ¹H NMR (400 MHz, DMSO) δ = 12.03 (s, 1H), 11.79 (s, 1H), 7.47-7.40 (m, 2H). 7.14-7.03 (m, 6H), 2.45-2.41 (m, 1H), 2.27 (s, 3H), 2.24-2.20 (m, 1H), 1.59-1.54 (m, 1H), 1.48-1.41 (m, 1H). |
| 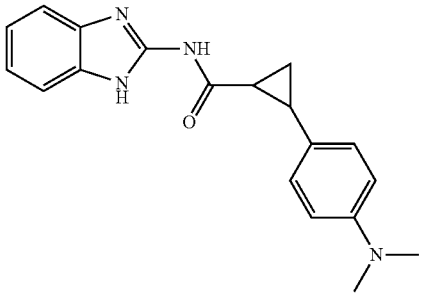 [SMILES: CN(C)c1ccc(C2CC2C(=O)Nc2nc3ccccc3[nH]2)cc1] | + | 2-(4-Dimethylamino-phenyl)-cyclopropane-carboxylic acid (1H-benzoimidazol-2-yl)-amide | ¹H NMR (400 MHz, DMSO) δ = 7.34 (d, J = 8, 1H), 7.23 (s, 2H), 7.19 (d, J = 7.6, 1H), 7.14 (d, J = 8.8, 2H), 7.09 (t, J = 7.6, 1H), 6.78 (t, J = 7.6, 1H), 6.71 (d, J = 8.8, 2H), 2.88 (s, 6H), 2.73-2.65 (m, 2H), 1.87-1.79 (m, 1H), 1.73-1.66 (m, 1H). |
| 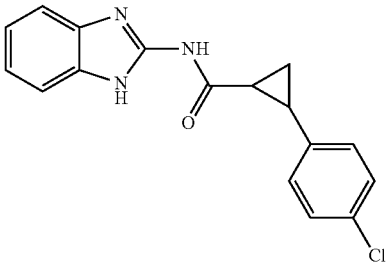 [SMILES: O=C(Nc1nc2ccccc2[nH]1)C1CC1c1ccc(Cl)cc1] | | 2-(4-Chloro-phenyl)-cyclopropane-carboxylic acid (1H-benzoimidazol-2-yl)-amide | ¹H NMR (400 MHz, DMSO) δ = 12.03 (s, 1H), 11.81 (s, 1H), 7.47-7.39 (m, 2H), 7.38-7.34 (m, 2H), 7.27-7.20 (m, 2H), 7.09-7.02 (m, 2H), 2.29-2.23 (m, 1H) 1.61-1.54 (m, 1H), 1.52-1.46 (m, 1H). |
| 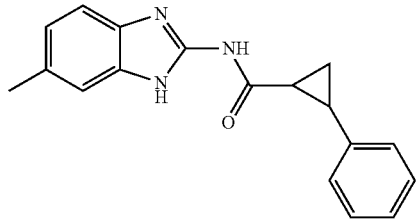 [SMILES: Cc1ccc2nc(NC(=O)C3CC3c3ccccc3)[nH]c2c1] | ++ | 2-Phenyl-cyclopropane-carboxylic acid (6-methyl-1H-benzoimidazol-2-yl)-amide | ¹H NMR (400 MHz, DMSO) δ = 11.90 (s, 1H), 11.75 (s, 1H), 7.34-7.27 (m, 3H), 7.26-7.17 (m, 3H), 6.89 (d, J = 8.0, 1H), 2.36 (s, 3H), 2.29-2.23 (m, 1H), 1.60-1.54 (m, 1H), 1.52-1.46 (m, 1H). |
| 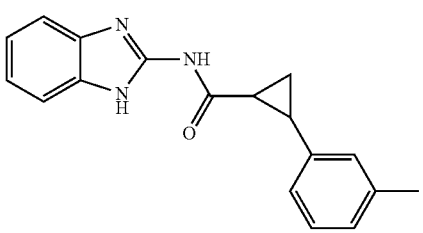 [SMILES: Cc1cccc(C2CC2C(=O)Nc2nc3ccccc3[nH]2)c1] | +++ | 2-m-Tolyl-cyclopropane-carboxylic acid (1H-benzoimidazol-2-yl)-amide | ¹H NMR (400 MHz, DMSO) δ = 12.03 (s, 1H), 11.78 (s, 1H), 7.48-7.39 (m, 2H), 7.23-7.16 (t, J = 7.6, 1H), 7.10-6.96 (m, 5H), 2.46-2.41 (m, 1H), 2.28 (s, 3H), 2.27-2.22 (m, 1H), 1.59-1.52 (m, 1H), 1.51-1.44 (m, 1H). |
| 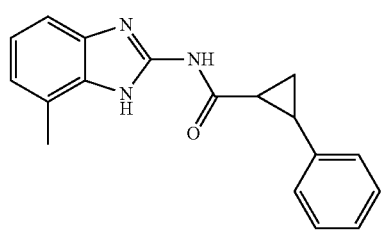 [SMILES: Cc1cccc2nc(NC(=O)C3CC3c3ccccc3)[nH]c12] | ++ | 2-Phenyl-cyclopropane-carboxylic acid (7-methyl-1H-benzoimidazol-2-yl)-amide | ¹H NMR (400 MHz, DMSO) δ = 12.00-11.95 (m, 2H), 7.35-7.26 (m, 3H), 7.25-7.18 (m, 3H), 7.00-6.93 (m, 1H), 6.92-6.87 (m, 1H), 2.45 (s, 3H), 2.27 (s, 3H), 2.27-2.20 (m, 1H), 1.60-1.53 (m, 1H), 1.51-1.46 (m, 1H). |

-continued

| | IC$_{50}$ (LPA2R) | Chemical Name | NMR |
|---|---|---|---|
| 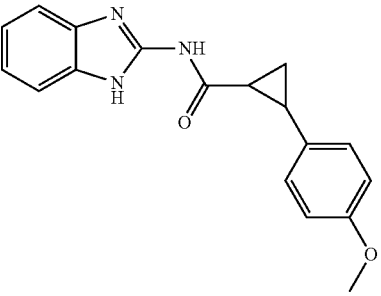 [SMILES: COc1ccc(C2CC2C(=O)Nc2nc3ccccc3[nH]2)cc1] | + | 2-(4-Methoxy-phenyl)-cyclopropane-carboxylic acid (1H-benzoimidazol-2-yl)-amide | $^1$H NMR (400 MHz, DMSO) δ = 11.60 (s, 1H), 7.48-7.39 (m, 2H), 7.17-7.10 (m, 2H), 7.09-7.03 (m, 2H), 6.91-6.85 (m, 2H), 3.72 (s, 3H), 2.45-2.40 (m, 1H), 2.23-2.17 (m, 1H), 1.56-1.48 (m, 1H), 1.46-1.38 (m, 1H) |
| 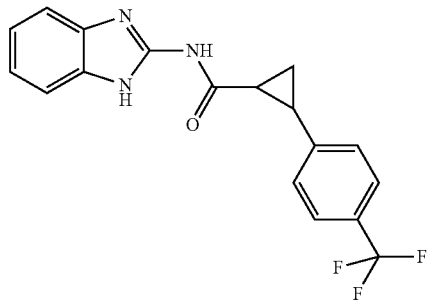 [SMILES: O=C(Nc1nc2ccccc2[nH]1)C1CC1c1ccc(C(F)(F)F)cc1] | + | 2-(4-Trifluoromethyl-phenyl)-cyclopropane-carboxylic acid (1H-benzoimidazol-2-yl)-amide | $^1$H NMR (400 MHz, DMSO) δ = 12.05 (s, 1H), 11.84 (s, 1H), 7.69-7.64 (m, 2H), 7.48-7.38 (m, 4H), 7.11-7.05 (m, 2H), 2.65-2.57 (m, 1H), 2.40-2.33 (m, 1H), 1.68-1.63 (m, 1H), 1.62-1.55 (m, 1H) |
| 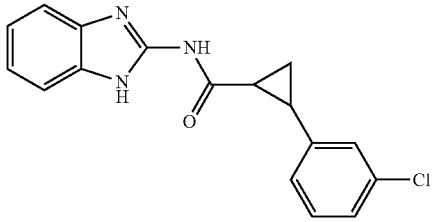 [SMILES: O=C(Nc1nc2ccccc2[nH]1)C1CC1c1cccc(Cl)c1] | ++ | 2-(3-Chloro-phenyl)-cyclopropane-carboxylic acid (1H-benzoimidazol-2-yl)-amide | $^1$H NMR (400 MHz, DMSO) δ = 12.07 (s, 1H), 11.85 (s, 1H), 7.50-7.38 (m, 3H), 7.36-7.27 (m, 2H), 7.26-7.21 (m, 1H), 7.11-7.05 (m, 2H), 2.70-2.64 (m, 1H), 2.22-2.16 (m, 1H), 1.63-1.56 (m, 2H), |
| 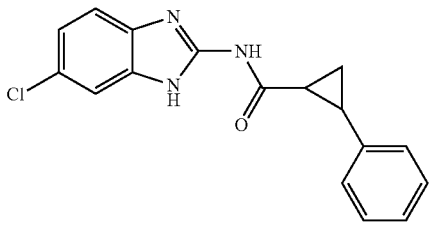 [SMILES: O=C(Nc1nc2ccc(Cl)cc2[nH]1)C1CC1c1ccccc1] | +++ | 2-Phenyl-cyclopropane-carboxylic acid (6-chloro-1H-benzoimidazol-2-yl)-amide | $^1$H NMR (400 MHz, DMSO) δ = 12.19 (s, 1H), 11.92 (s, 1H), 7.50-7.37 (m, 2H), 7.35-7.28 (m, 2H), 7.25-7.17 (m, 3H), 7.13-7.07 (m, 1H), 2.30-2.25 (m, 1H), 1.62-1.56 (m, 1H), 1.55-1.48 (m, 1H) |
| 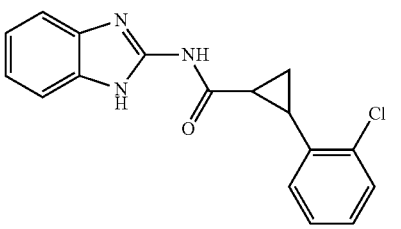 [SMILES: O=C(Nc1nc2ccccc2[nH]1)C1CC1c1ccccc1Cl] | +++ | 2-(2-Chloro-phenyl)-cyclopropane-carboxylic acid (1H-benzoimidazol-2-yl)-amide | $^1$H NMR (400 MHz, DMSO) δ = 12.03 (s, 1H), 11.78 (s, 1H), 7.50-7.38 (m, 2H), 7.37-7.25 (m, 3H), 7.22-7.16 (m, 1H), 7.10-7.04 (m, 2H), 2.35-2.28 (m, 1H), 1.62-1.51 (m, 2H), |
| 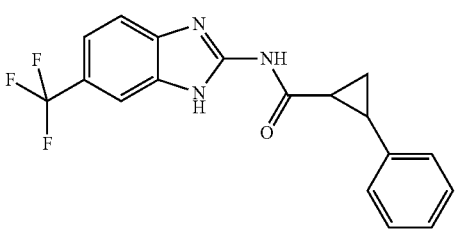 [SMILES: O=C(Nc1nc2ccc(C(F)(F)F)cc2[nH]1)C1CC1c1ccccc1] | +++ | 2-Phenyl-cyclopropane-carboxylic acid (6-trifluoromethyl-1H-benzoimidazol-2-yl)-amide | $^1$H NMR (400 MHz, DMSO) δ = 12.45 (d, J = 9.2, 1H), 12.05 (d, J = 8.8, 1H), 7.70 (d, J = 23.6, 1H), 7.61 (dd, J = 8.4, J = 23.6, 1H), 7.41 (d, J = 8, 1H), 7.35-7.28 (m, 2H), 7.26-7.20 (m, 3H), 2.34-2.27 (m, 1H), 1.62-1,56 (m, 1H), 1.55-1.48 (m, 1H). |

-continued

| IC$_{50}$ (LPA2R) | Chemical Name | NMR |
|---|---|---|
| + | 2-Phenyl-cyclopropane-carboxylic acid (1H-benzoimidazol-2-yl)-methyl-amide | $^1$H NMR (400 MHz, DMSO) δ = 12.45 (s, 1H), 7.51-7.45 (m, 2H), 7.30-7.26 (m, 2H), 7.25-7.16 (m, 3H), 7.15-7.09 (m, 2H), 3.61 (s, 3H), 1.63-1.57 (m, 1H), 1.50-1.38 (m, 1H). |
| | 2-Phenyl-cyclopropane-carboxylic acid (1-methyl-1H-benzoimidazol-2-yl)-amide | $^1$H NMR (400 MHz, DMSO) δ = 12.42 (s, 1H), 7.59-7.38 (m, 2H), 7.36-7.12 (m, 7H), 3.57 (s, 3H), 2.44-2.36 (m, 1H), 2.04-1.97 (m, 1H), 1.57-1.51 (m, 1H), 1.48-1.40 (m, 1H). |
| + | 2-Phenyl-cyclopropane-carboxylic acid [5-(propane-1-sulfonyl)-1H-benzoimidazol-2-yl]-amide | $^1$H NMR (500 MHz, DMSO, TFA) δ = 8.11 (t, J = 5.3, 1H), 7.84 (dt, J = 22.5, 5.0, 2H), 7.29-7.22 (m, 2H), 7.17 (dd, J = 7.4, 3.6, 3H), 3.23-3.11 (m, 2H), 2.65-2.55 (m, 1H), 2.34-2.23 (m, 1H), 1.73 (dt, J = 9.5, 4.9, 1H), 1.67-1.46 (m, 3H), 0.84 (m, 3H). |
| ++ | {2-[(2-Phenyl-cyclopropane-carbonyl)-amino]-1H-benzoimidazol-5-ylmethyl}-carbamic acid tert-butyl ester | $^1$H NMR (400 MHz, THF) δ = 11.35 (d, J = 85.3, 2H), 7.34 (s, 1H), 7.30-7.20 (m, 3H), 7.20-7.10 (m, 3H), 7.00 (dd, J = 8.2, 1.5, 1H), 4.27 (d, J = 5.9, 2H), 2.61-2.49 (m, 1H), 2.46 (s, 2H), 2.19-2.01 (m, 1H), 1.67 (ddd, J = 9.3, 5.1, 4.3, 1H), 1.50-1.30 (s, 9H). |
| + | 2-Phenyl-cyclopropane-carboxylic acid (5-aminomethyl-1H-benzoimidazol-2-yl)-amide | |
| +++ | 2-Phenyl-cyclopropane-carboxylic acid (5,6-dimethyl-1H-benzoimidazol-2-yl)-amide | $^1$H NMR (400 MHz, DMSO) δ = 11.80 (d, 1H), 11.72 (d, 1H), 7.34-7.27 (m, 2H), 7.26-7.16 (m, 5H), 2.48-2.43 (m, 1H), 2.26 (s, 6H), 2.25-2.22 (m, 1H), 1.59-1.52 (m, 1H), 1.51-1.44 (m, 1H). |
| ++ | 2-Phenyl-cyclopropane-carboxylic acid (5,6-dichloro-1H-benzoimidazol-2-yl)-amide | $^1$H NMR (400 MHz, DMSO) δ = 12.32 (d, 1H), 12.2 (d, 1H) 7.65 (d, 2H), 7.35-7.28 (m, 2H), 7.26-7.17 (m, 3H), 2.31-2.22 (m, 1H), 1.63-1.57 (m, 1H), 1.56-1.49 (m, 1H). |

-continued

| | IC$_{50}$ (LPA2R) | Chemical Name | NMR |
|---|---|---|---|
| 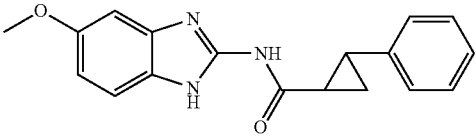 [SMILES: COc1ccc2[nH]c(NC(=O)C3CC3c3ccccc3)nc2c1] | +++ | 2-Phenyl-cyclopropane-carboxylic acid (5-methoxy-1H-benzoimidazol-2-yl)-amide | |
| 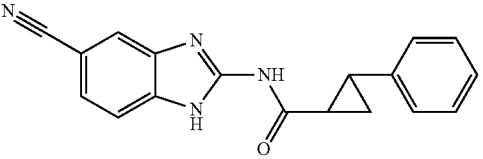 [SMILES: N#Cc1ccc2[nH]c(NC(=O)C3CC3c3ccccc3)nc2c1] | +++ | 2-Phenyl-cyclopropane-carboxylic acid (5-cyano-1H-benzoimidazol-2-yl)-amide | $^1$H NMR (400 MHz, DMSO) δ = 12.53 (d, J = 17.2, 1H), 12.08 (d, J = 28, 1H), 7.86 (d, J = 24.8, 1H), 7.62-7.47 (m, 2H), 7.33-7.30 (m, 2H), 7.24-7.19 (m, 3H), 2.33-2.27 (m, 1H), 1.62-1.56 (m, 1H), 1.55-1.48 (m, 1H). |
| 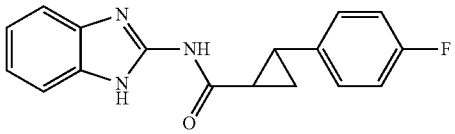 [SMILES: O=C(Nc1nc2ccccc2[nH]1)C1CC1c1ccc(F)cc1] | +++ | 2-(4-Fluoro-phenyl)-cyclopropane-carboxylic acid (1H-benzoimidazol-2-yl)-amide | $^1$H NMR (400 MHz, DMSO) δ = 12.03 (s, 1H), 11.79 (s, 1H), 7.42 (d, J = 18.0, 2H), 7.28-7.23 (m, 2H), 7.17-7.11 (m, 2H), 7.08-7.04 (m, 2H), 2.28-2.22 (m, 1H), 1.59-1.56 (m, 1H), 1.50-1.45 (m, 1H). |
| 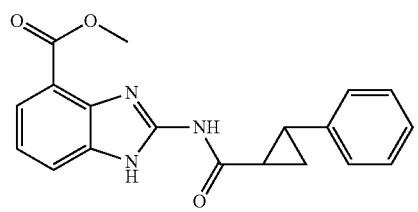 [SMILES: COC(=O)c1cccc2[nH]c(NC(=O)C3CC3c3ccccc3)nc12] | ++ | 2-[(2-Phenyl-cyclopropane-carbonyl)-amino]-1H-benzoimidazole-4-carboxylic acid methyl ester | $^1$H NMR (400 MHz, DMSO) δ = 12.23 (d, 1H), 11.77 (s, 1H), 7.78-7.70 (m, 2H), 7.34-7.15 (m, 6H), 2.60-2.54 (m, 1H), 2.33-2.27 (m, 1H), 1.67-1.60 (m, 1H), 1.59-1.52 (m, 1H). |
| 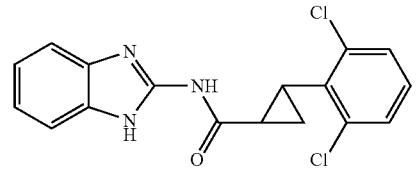 [SMILES: O=C(Nc1nc2ccccc2[nH]1)C1CC1c1c(Cl)cccc1Cl] | | 2-(2,6-Dichloro-phenyl)-cyclopropane-carboxylic acid (1H-benzoimidazol-2-yl)-amide | $^1$H NMR (400 MHz, DMSO) δ = 12.09 (d, 1H), 12.00 (d, 1H), 7.51-7.39 (m, 4H), 7.46-7.43 (m, 1H), 7.11-7.06 (m, 2H), 2.44-2.37 (m, 1H), 2.29-2.24 (m, 1H), 1.74-1.68 (m, 1H), 1.53-1.47 (m, 1H). |
| 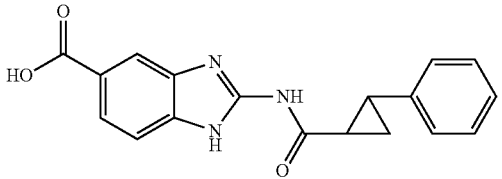 [SMILES: O=C(O)c1ccc2[nH]c(NC(=O)C3CC3c3ccccc3)nc2c1] | | 2-[(2-Phenyl-cyclopropane-carbonyl)-amino]-1H-benzoimidazole-5-carboxylic acid | $^1$H NMR (400 MHz, DMSO) δ = 12.33 (s, 1H), 11.99 (d, J = 8, 1H), 8.08-8.04 (m, 1H), 7.75-7.70 (m, 1H), 7, 45 (s, 1H), 7.35-7.28 (m, 2H), 7.25-7.14 (m, 3H), 2.31-2.26 (m, 1H), 1.63-1.58 (m, 1H), 1.53-1.47 (m, 1H). |
| 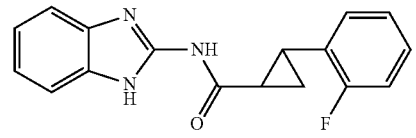 [SMILES: O=C(Nc1nc2ccccc2[nH]1)C1CC1c1ccccc1F] | ++ | 2-(2-Fluoro-phenyl)-cyclopropane-carboxylic acid (1H-benzoimidazol-2-yl)-amide | |
| 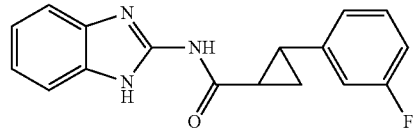 [SMILES: O=C(Nc1nc2ccccc2[nH]1)C1CC1c1cccc(F)c1] | +++ | 2-(3-Fluoro-phenyl)-cyclopropane-carboxylic acid (1H-benzoimidazol-2-yl)-amide | |
| 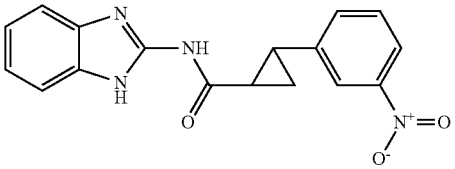 [SMILES: O=C(Nc1nc2ccccc2[nH]1)C1CC1c1cccc([N+](=O)[O-])c1] | +++ | 2-(3-Nitro-phenyl)-cyclopropane-carboxylic acid (1H-benzoimidazol-2-yl)-amide | $^1$H NMR (400 MHz, DMSO) δ = 12.06 (s, 1H), 8.10-8.01 (m, 2H), 7.74-7.60 (m, 2H), 7.49-7.38 (m, 2H), 7.11-7.03 (m, 2H), 2.72-2.67 (m, 1H), 2.41-2.37 (m, 1H), 1.68-1.58 (m, 2H), |

-continued

| Structure | IC₅₀ (LPA2R) | Chemical Name | NMR |
|---|---|---|---|
| | +++ | 2-Phenyl-cyclopropane-carboxylic acid (1H-benzoimidazol-2-yl)-amide | $^1$H NMR (400 MHz, DMSO) δ = 12.03 (s, 1H), 11.79 (s, 1H), 7.49-7.37 (m, 2H), 7.34-7.28 (m, 2H), 7.25-7.18 (m, 3H), 7.10-7.3 (m, 3H), 2.30-2.25 (m, 1H), 1.60-1.55 (m, 1H), 1.52-1.47(m, 1H), |
| | | 2-(4-tert-Butyl-phenyl)-cyclopropane-carboxylic acid (1H-benzoimidazol-2-yl)-amide | $^1$H NMR (400 MHz, DMSO) δ = 12.03 (s, 1H), 11.80 (s, 1H), 7.49-7.36 (m, 2H), 7.34-7.29 (m, 2H), 7.16-7.10 (m, 3H), 7.09-7.03 (m, 2H), 2.49-2.42 (m, 1H), 2.27-2.21 (m, 1H), 1.59-1.54 (m, 1H), 1.49-1.44 (m, 1H), 1.25 (s, 9H) |
| | | 2-(3-Methoxy-phenyl)-cyclopropane-carboxylic acid (1H-benzoimidazol-2-yl)-amide | $^1$H NMR (400 MHz, DMSO) δ = 11.90-11.65 (m, 2H), 7.40-7.33 (m, 2H), 7.13 (t, J = 7.6, 1H), 7.06-6.99 (m, 2H), 6.86-6.80 (m, 2H), 6.73-6.68 (m, 1H), 3.67 (s, 1H), 2.68-2.59 (m, 1H), 2.44-2.38 (m, 1H), 1.69-1.64 (m, 1H), 1.43-1.37 (m, 1H), |
| | +++ | 2-(3-Bromo-phenyl)-cyclopropane-carboxylic acid (1H-benzoimidazol-2-yl)-amide | $^1$H NMR (400 MHz, DMSO) δ = 12.03 (s, 1H), 11.78 (d, 1H), 7.50-7.41 (m, 4H), 7.30-7.21 (m, 2H), 7.09-7.05 (m, 2H), 2.33-2.29 (m, 1H), 1.62-1.51 (m, 2H), |
| | +++ | 2-(5-Bromo-2-fluoro-phenyl)-cyclopropane-carboxylic acid (1H-benzoimidazol-2-yl)-amide | $^1$H NMR (400 MHz, DMSO) δ = 12.05 (s, 1H), 11.83 (s, 1H), 7.49-7.41 (m, 4H), 7.20 (t, J = 2, 1H), 7.09-7.05 (m, 2H), 2.58-2.53 (m, 1H), 2.35-2.30 (m, 1H), 1.65-1.53 (m, 2H), |
| | ++ | 2-(3-Cyano-phenyl)-cyclopropane-carboxylic acid (1H-benzoimidazol-2-yl)-amide | $^1$H NMR (400 MHz, DMSO/) δ = 12.04 (s, 1H), 11.82 (s, 1H), 7.72-7.66 (m, 1H), 7.63-7.59 (m, 1H), 7.57-7.47 (m, 3H), 7.22-7.14 (m, 2H), 2.65-2.59 (m, 1H), 2.37-2.31 (m, 1H), 1.68-1.62 (m, 2H). |
| | ++ | 2-(2,3-Dichloro-phenyl)-cyclopropane-carboxylic acid (1H-benzoimidazol-2-yl)-amide | $^1$H NMR (400 MHz, DMSO/) δ = 12.07 (s, 1H), 11.89 (s, 1H), 7.58-7.53 (m, 1 H), 7.48-7.40 (m, 2H), 7.36 (t, J = 8, 1H), 7.28-7.22 (m, 1H), 7.12-7.04 (m 2H), 2.73-2.67 (m, 1H), 2.22-2.17 (m, 1H), 1.65-1.57 (m, 2H), |
| | ++ | 2-(3-Dimethylamino-phenyl)-cyclopropane-carboxylic acid (1H-benzoimidazol-2-yl)-amide | $^1$H NMR (400 MHz, DMSO) δ = 12.03 (s, 1H), 11.79 (s, 1H), 7.50-7.45 (m, 2H), 7.14-7.05 (m, 3H), 6.58 (t, J = 2.4, 2H), 6.44 (d, J = 7.2, 1H), 2.46-2.40 (m, 1H), 2.29-2.23 (m, 1H), 1.56-1.50 (m, 1H), 1.49-1.43 (m, 1H) |

-continued

| | IC$_{50}$ (LPA2R) | Chemical Name | NMR |
|---|---|---|---|
| (indazole structure) | | 2-Phenyl-cyclopropane-carboxylic acid (1H-indazol-3-yl)-amide | $^1$H NMR (400 MHz, DMSO) δ = 12.70 (s, 1H), 10.66 (s, 1H), 7.80 (d, J = 8, 1H), 7.44-7.39 (m, 1H), 7.36-7.27 (m, 3H), 7.24-7.18 (m, 3H) 7.08-7.00 (m, 1H), 2.46-2.39 (m, 1H), 2.29-2.22 (m, 1H), 1.55-1.48 (m, 1H), 1.42-1.37 (m, 1H) |
| (benzimidazole-CF3 structure) | | 2-(2-Trifluoromethyl-phenyl)-cyclopropane-carboxylic acid (1H-benzoimidazol-2-yl)-amide | $^1$H NMR (400 MHz, DMSO) δ = 12.08 (s, 1H), 11.86 (s, 1H), 7.38 (d, J = 8, 1H), 7.66 (t, J = 7.6, 1H), 7.50-7.36 (m, 4H), 7.10-7.04 (m, 1H), 2.73-2.67 (m, 1H), 2.29-2.23 (m, 1H), 1.77-1.69 (m, 1H), 1.62-1.55 (m, 1H) |
| (5-ethyl benzimidazole structure) | +++ | 2-Phenyl-cyclopropane-carboxylic acid (5-ethyl-1H-benzoimidazol-2-yl)-amide | $^1$H NMR (400 MHz, DMSO) δ = 11.90 (s, 1H), 11.75 (s, 1H), 7.36-7.28 (m, 3H), 7.27-7.17 (m, 4H), 6.95-6.90 (m, 1H), 2.66 (dd, J = 7.6, J = 14.8, 2H), 2.29-2.24 (m, 1H), 1.60-1.53 (m, 1H), 1.51-1.46 (m, 1H), 1.20 (t, J = 7.6, 3H) |
| (4,6-dichloro benzimidazole structure) | ++ | 2-Phenyl-cyclopropane-carboxylic acid (4,6-dichloro-1H-benzoimidazol-2-yl)-amide | $^1$H NMR (400 MHz, DMSO) δ = 12.46 (s, 1H), 12.25 (s, 1H), 7.46 (d, J = 1.8, 1H), 7.34-7.29 (m, 2H), 7.27 (d, J = 1.8, 1H), 7.24-7.18 (m, 3H), 2.26-2.20 (m, 1H), 1.62-1.57 (m, 1H), 1.56-1.50 (m, 1H) |
| (dimethylamino structure) | ++ | 2-(2-Dimethylamino-phenyl)-cyclopropane-carboxylic acid (1H-benzoimidazol-2-yl)-amide | |
| (6-chloro imidazopyridine structure) | ++++ | 2-Phenyl-cyclopropane-carboxylic acid (6-chloro-3H-imidazo[4,5-b]pyridin-2-yl)-amide | $^1$H NMR (400 MHz, DMSO, TFA) δ = 8.61 (d, J = 2.1, 1H), 8.24 (d, J = 2.1, 1H), 7.30 (ddd, J = 12.5, 9.7, 6.9, 5H), 2.69-2.60 (m, 1H), 2.49-2.36 (m, 1H), 1.77 (dt, J = 9.4, 4.8, 1H), 1.68-1.58 (m, 1H), . |
| (imidazo[4,5-b]pyridine structure) | +++ | 2-Phenyl-cyclopropane-carboxylic acid (3H-imidazo[4,5-b]pyridin-2-yl)-amide | $^1$H NMR (500 MHz, DMSO, TFA) δ = 8.45 (d, J = 6.1, 1H), 8.39 (d, J = 7.8, 1H), 7.56 (dd, J = 7.8, 6.2, 1H), 7.37-7.30 (m, 2H), 7.25 (dd, J = 7.2, 4.6, 3H), 2.68-2.60 (m, 1H), 2.45-2.38 (m, 1H), 1.73 (dt, J = 9.4, 4.8, 1H), 1.66-1.56 (m, 1H). |
| (imidazo[4,5-c]pyridine structure) | | 2-Phenyl-cyclopropane-carboxylic acid (3H-imidazo[4,5-c]pyridin-2-yl)-amide | $^1$H NMR (400 MHz, DMSO, TFA) δ = 9.04 (s, 1H), 8.51 (dd, J = 6.5, 0.7, 1H), 7.97 (d, J = 6.5, 1H), 7.38-7.29 (m, 2H), 7.29-7.18 (m, 3H), 2.65-2.57 (m, 1H), 2.39 (ddd, J = 11.7, 7.4, 3.5, 1H), 1.69 (dt, J = 9.4, 4.6, 1H), 1.59 (dt, J = 10.9, 7.2, 1H). |

-continued

| Structure | IC$_{50}$ (LPA2R) | Chemical Name | NMR |
|---|---|---|---|
| | +++ | 2-Phenyl-cyclopropane-carboxylic acid (4-nitro-1H-benzoimidazol-2-yl)-amide | $^1$H NMR (400 MHz, DMSO, TFA) δ = 8.05 (d, J = 8.3, 1H), 7.95 (dd, J = 7.9, 0.8, 1H), 7.38 (t, J = 8.1, 1H), 7.35-7.27 (m, 2H), 7.23 (dt, J = 7.0, 2.8, 3H), 2.65-2.55 (m, 1H), 2.38-2.30 (m, 1H), 1.66 (dt, J = 9.3, 4.7, 1H), 1.58 (ddd, J = 8.1, 6.7, 4.4, 1H). |
| | ++ | 2-Phenyl-cyclopropane-carboxylic acid (4-nitro-6-trifluoromethyl-1H-benzoimidazol-2-yl)-amide | $^1$H NMR (400 MHz, DMSO, TFA) δ = 8.25 (d, J = 0.9, 1H), 8.21 (d, J = 1.0, 1H), 7.38-7.29 (m, 2H), 7.29-7.20 (m, 3H), 2.68-2.60 (m, 1H), 2.44-2.35 (m, 1H), 1.71 (dt, J = 9.4, 4.5, 1H), 1.57 ddd (J = 8.2, 6.7, 4.4, 1H). |
| | ++++ | 2-(3-Fluoro-phenyl)-cyclopropane-carboxylic acid (6-chloro-3H-imidazo[4,5-b]pyridin-2-yl)-amide | $^1$H NMR (400 MHz, DMSO, TFA) δ = 8.47 (d, J = 2.1, 1H), 8.15 (d, J = 2.1, 1H), 7.26 (td, J = 7.9, 6.2, 1H), 7.05-6.87 (m, 3H), 2.57 (ddd, J = 10.9, 7.4, 4.1, 1H), 2.42-2.30 (m, 1H), 1.68 (dt, J = 9.6, 4.8, 1H), 1.54 (ddd, J = 8.1, 6.7, 4.6, 1H). |
| enantiomer | + | enantiomer-2-Phenyl-cyclopropane-carboxylic acid (1H-benzoimidazol-2-yl)-amide | $^1$H NMR (400 MHz, DMSO, TFA) δ = 7.74-7.67 (m, 2H), 7.49-7.41 (m, 2H), 7.35 (dd, J = 9.4, 5.5, 2H), 7.31-7.22 (m, 3H), 2.65 (ddd, J = 14.5, 9.2, 5.9, 1H), 2.45-2.32 (m, 1H), 1.78 (dt, J = 9.5, 4.7, 1H), 1.74-1.63 (m, 1H). |
| enantiomer | ++++ | enantiomer-2-Phenyl-cyclopropane-carboxylic acid (1H-benzoimidazol-2-yl)-amide | $^1$H NMR (400 MHz, DMSO, TFA) δ = 7.74-7.66 (m, 2H), 7.48-7.39 (m, 2H), 7.39-7.31 (m, 2H), 7.26 (dd, J = 10.0, 4.3, 3H), 2.71-2.62 (m, 1H), 2.43-2.33 (m, 1H), 1.78 (dt, J = 9.5, 4.7, 1H), 1.74-1.65 (m, 1H). |
| enantiomer | +++ | enantiomer-2-(2-Chloro-phenyl)-cyclopropane-carboxylic acid (1H-benzoimidazol-2-yl)-amide | $^1$H NMR (400 MHz, DMSO, TFA) δ = 7.52-7.41 (m, 4H), 7.35-7.28 (m, 2H), 7.24 (dd, J = 7.3, 2.0, 1H), 7.15 (dd, J = 5.9, 3.2, 2H), 2.78-2.63 (m, 1H), 2.30-2.14 (m, 1H), 1.71-1.53 (m, 2H). |

| IC$_{50}$ (LPA2R) | Chemical Name | NMR |
|---|---|---|
| +++ | 2-Phenyl-cyclopropane-carboxylic acid (4-amino-1H-benzoimidazol-2-yl)-amide | |
| +++ | 2-Phenyl-cyclopropane-carboxylic acid (4-chloro-3H-imidazo[4,5-c]pyridin-2-yl)-amide | $^1$H NMR (400 MHz, DMSO, TFA) δ = 8.28 (d, J = 5.9, 1H), 7.76 (d, J = 5.9, 1H), 7.33 (dd, J = 9.5, 5.6, 2H), 7.29-7.19 (m, 3H), 2.68-2.57 (m, 1H), 2.39-2.29 (m, 1H), 1.69 (dt, J = 9.4, 4.7, 1H), 1.58 (td, J = 8.1, 4.4, 1 H). |
| ++++ | 2-Phenyl-cyclopropane-carboxylic acid (6-bromo-3H-imidazo[4,5-b]pyridin-2-yl)-amide | $^1$H NMR (400 MHz, DMSO, TFA) δ = 8.56 (d, J = 1.9, 1H), 8.27 (d, J = 1.9, 1H), 7.30-7.20 (m, 2H), 7.20-7.12 (m, 3H), 2.59-2.54 (m, 1H), 2.39-2.29 (m, 1H), 1.68 (dt, J = 9.5, 4.7, 1H), 1.53 (ddd, J = 8.0, 6.7, 4.5, 1H). |
| ++++ | 2-(3-Fluoro-phenyl)-cyclopropane-carboxylic acid (6-cyano-1H-benzoimidazol-2-yl)-amide | $^1$H NMR (400 MHz, DMSO, TFA) δ = 8.10 (d, J = 0.7, 1H), 7.88-7.81 (m, 1 H), 7.77 (dd, J = 8.2, 1.2, 1H), 7.36 (td, J = 8.0, 6.2, 1H), 7.16-6.96 (m, 3H), 2.71 (ddd, J = 9.4, 7.4, 4.1, 1H), 2.43 (ddd, J = 9.3, 5.3, 4.0, 1H), 1.82 (dt, J = 9.6, 4.9, 1H), 1.70 (ddd, J = 8.1, 6.8, 4.7, 1H). |
| +++ | 2-(2-Chloro-phenyl)-cyclopropane-carboxylic acid (6-trifluoromethyl-1H-benzoimidazol-2-yl)-amide | $^1$H NMR (400 MHz, DMSO, TFA) δ = 8.01 (s, 1H), 7.88 (d, J = 8.5, 1H), 7.74 (d, J = 8.5, 1H), 7.48 (dd, J = 7.6, 1.3, 1H), 7.38-7.22 (m, 3H), 2.90 (ddd, J = 9.1, 7.2, 4.3, 1H), 2.35-2.21 (m, 1H), 1.89-1.69 (m, 2H). |
| + | 2-Phenyl-cyclopropane-carboxylic acid (9H-purin-8-yl)-amide | $^1$H NMR (400 MHz, DMSO, TFA) δ = 9.12 (d, J = 1.2, 1H), 8.89 (d, J = 1.3, 1H), 7.31-7.21 (m, 2H), 7.17 (dd, J = 7.2, 5.2, 3H), 2.58-2.50 (m, 1H), 2.42-2.35 (m, 1H), 1.68 (dt, J = 9.5, 4.8, 1H), 1.59-1.48 (m, 1H). |

-continued

| | IC$_{50}$ (LPA2R) | Chemical Name | NMR |
|---|---|---|---|
| enantiomer | | enantiomer-2-{[2-(2-Chloro-phenyl)-cyclopropane-carbonyl]-amino}-3H-benzoimidazole-4-carboxylic acid methyl ester | $^1$H NMR (400 MHz, DMSO, TFA) δ = 8.02 (ddd, J = 11.5, 8.0, 1.0, 2H), 7.56 (t, J = 8.0, 1H), 7.52-7.44 (m, 1H), 7.38-7.24 (m, 3H), 4.05 (s, 3H), 2.88 (ddd, J = 9.1, 7.2, 4.3, 1H), 2.34 (dt, J = 8.2, 5.1, 1H), 1.79 (m, 2H). |
| enantiomer | ++++ | enantiomer-2-Phenyl-cyclopropane-carboxylic acid (6-chloro-3H-imidazo[4,5-b]pyridin-2-yl)-amide | $^1$H NMR (400 MHz, DMSO, TFA) δ = 8.63 (d, J = 10.3, 1H), 8.22 (d, J = 10.3, 2.1, 1H), 7.40-7.31 (m, 2H), 7.30-7.17 (m, 3H), 2.70-2.59 (m, 1H), 2.42 (dt, J = 5.3, 4.6, 1H), 1.76 (dt, J = 9.5, 4.7, 1H), 1.64 (td, J = 8.0, 4.5, 1H). |
| enantiomer | + | trans-2-Phenyl-cyclopropane-carboxylic acid (6-chloro-3H-imidazo[4,5-b]pyridin-2-yl)-amide | $^1$H NMR (400 MHz, DMSO, TFA) δ = 8.61 (d, J = 2.1, 1H), 8.23 (d, J = 2.1, 1H), 7.40-7.31 (m, 2H), 7.30-7.17 (m, 3H), 2.64 (ddd, J = 11.1, 7.5, 4.2, 2H), 2.41 (dt, J = 5.3, 4.6, 1H), 1.75 (dt, J = 9.1, 4.7, 1H), 1.64 (td, J = 8.1, 4.4, 1H). |
| enantiomer | ++ | enantiomer-2-(2-Chloro-phenyl)-cyclopropane-carboxylic acid (6-chloro-1H-benzoimidazol-2-yl)-amide | $^1$H NMR (400 MHz, DMSO, TFA) δ = 7.75-7.65 (m, 2H), 7.54-7.45 (m, 2H), 7.40-7.20 (m, 3H), 2.91-2.78 (m, 1H), 2.35-2.20 (m, 1H), 1.88-1.70 (m, 2H). |
| enantiomer | +++ | enantiomer-2-Phenyl-cyclopropane-carboxylic acid (6-cyano-1H-benzoimidazol-2-yl)-amide | $^1$H NMR (400 MHz, DMSO, TFA) δ = 8.04 (d, J = 0.5, 1H), 7.80-7.69 (m, 2H), 7.39-7.29 (m, 2H), 7.29-7.18 (m, 3H), 2.69-2.58 (m, 1H), 2.42-2.31 (m, 1H), 1.72 (dt, J = 9.4, 4.8, 1H), 1.66 (td, J = 8.0, 4.5, 1H). |
| enantiomer | + | enantiomer-2-Phenyl-cyclopropane-carboxylic acid (6-cyano-1H-benzoimidazol-2-yl)-amide | $^1$H NMR (400 MHz, DMSO, TFA) δ = 8.04 (d, J = 0.5, 1H), 7.80-7.69 (m, 2H), 7.39-7.29 (m, 2H), 7.29-7.18 (m, 3H), 2.69-2.58 (m, 1H), 2.42-2.31 (m, 1H), 1.72 (dt, J = 9.4, 4.8, 1H), 1.66 (td, J = 8.0, 4.5, 1H). |

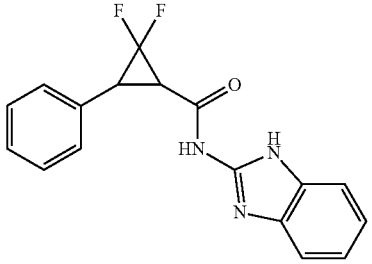 [SMILES: O=C(Nc1nc2ccccc2[nH]1)C1C(c2ccccc2)C1(F)F]

| IC$_{50}$ (LPA2R) | Chemical Name | NMR |
|---|---|---|
| +++ | 2-(2-Chloro-phenyl)-cyclopropane-carboxylic acid (6-cyano-1H-benzoimidazol-2-yl)-amide | $^1$H NMR (400 MHz, DMSO/TFA) δ = 8.11 (dd, J = 1.5, 0.7, 1H), 7.84 (dd, J = 8.4, 0.7, 1H), 7.79 (dd, J = 8.4, 1.5, 1H), 7.48 (dd, J = 7.6, 1.5, 1H), 7.39-7.22 (m, 3H), 2.95-2.83 (m, 1H), 2.30 (m, 1H), 1.79 (m, 2H). |
| enantiomer + | enantiomer-2-Phenyl-cyclopropane-carboxylic acid [5-(2-pyrrolidin-1-yl-ethoxy)-1H-benzoimidazol-2-yl]-amide | $^1$H NMR (400 MHz, DMSO/TFA) δ = 7.64 (d, J = 8.9, 1H), 7.38-7.29 (m, 3H), 7.29-7.22 (m, 3H), 7.14 (dd, J = 8.9, 2.4, 1H), 4.49-4.34 (m, 2H), 3.79-3.60 (m, 5H), 3.25-3.17 (m, 2H), 2.66 (ddd, J = 12.3, 8.1, 4.7, 1H), 2.41-2.31 (m, 1H), 2.11 (m, 2H), 2.05-1.89 (m, 2H), 1.79 (dt, J = 9.5, 4.8, 1H), 1.67 (td, J = 8.0, 4.6, 1H). |
| +++ | 2,2-Difluoro-3-phenyl-cyclopropane-carboxylic acid (6-chloro-1H-benzoimidazol-2-yl)-amide | $^1$H NMR (400 MHz, DMSO/TFA) δ = 7.76-7.70 (m, 2H), 7.57-7.31 (m, 6H), 3.91-3.73 (m, 1H), 3.58-3.41 (m, 1H). |
| ++ | 2,2-Difluoro-3-phenyl-cyclopropane-carboxylic acid (6-trifluoromethyl-1H-benzoimidazol-2-yl)-amide | $^1$H NMR (400 MHz, DMSO/TFA) δ = 8.03 (s, 1H), 7.90 (d, J = 8.5, 1H), 7.75 (dd, J = 8.6, 1.2, 1H), 7.57-7.22 (m, 5H), 3.88-3.79 (m, 1H), 3.57-3.50 (m, 1H) |
| ++ | 2,2-Difluoro-3-phenyl-cyclopropane-carboxylic acid (6-cyano-1H-benzoimidazol-2-yl)-amide | $^1$H NMR (400 MHz, DMSO/TFA) δ = 8.12 (dd, J = 1.5, 0.8, 1H), 7.85 (dd, J = 7.6, 3.6, 1H), 7.78 (dd, J = 7.6, 1.5, 1H), 7.58-7.27 (m, 5H), 3.85 (m, 1H), 3.57-3.45 (m, 1H). |

-continued

| IC$_{50}$ (LPA2R) | Chemical Name | NMR |
|---|---|---|
| + | 1-({2-[(2-Phenyl-cyclopropane-carbonyl)-amino]-1H-benzoimidazol-4-ylamino)-methyl)-pyrrolidine-3-carboxylic acid benzyl ester | |
| + | 2-Phenyl-cyclopropane-carboxylic acid {4-[(1-benzyl-piperidin-4-ylmethyl)-amino]-1H-benzoimidazol-2-yl}-amide | $^1$H NMR (500 MHz, DMSO/TFA) δ = 7.60-7.44 (m, 5H), 7.39-7.29 (m, 2H), 7.29-7.17 (m, 5H), 6.90 (d, J = 8.1, 1H), 4.32 (s, 2H), 3.49 (d, J = 12.2, 2H), 3.19 (d, J = 6.5, 2H), 3.03 (t, J = 12, 2H), 2.68-2.62 (m, 1H), 2.42-2.31 (m, 1H), 2.11-2.02 (m, 2H), 2.01-1.89 (m, 1H), 1.83-1.74 (m, 1H), 1.71-1.61 (m, 1H), 1.54 (m, 2H). |
| n.d. | enantiomer-2,2-Difluoro-3-phenyl-cyclopropane-carboxylic acid (6-chloro-1H-benzoimidazol-2-yl)-amide | $^1$H NMR (400 MHz, DMSO/TFA) δ = 7.76-7.70 (m, 2H), 7.57-7.31 (m, 6H), 3.91-3.73 (m, 1H), 3.58-3.41 (m, 1H). |
| n.d. | 2,2-Difluoro-3-phenyl-cyclopropane-carboxylic acid (6-chloro-1H-benzoimidazol-2-yl)-amide | $^1$H NMR (400 MHz, DMSO/TFA) δ = 776-7.70 (m, 2H), 7.57-7.31 (m, 6H), 3.91-3.73 (m, 1H), 3.58-3.41 (m, 1H). |

| IC$_{50}$ (LPA2R) | Chemical Name | NMR |
|---|---|---|
| | 2,2-Dimethyl-3-phenyl-cyclopropane-carboxylic acid (1H-benzoimidazol-2-yl)-amide | $^1$H NMR (400 MHz, DMSO/TFA) δ = 7.75-7.68 (m, 2H), 7.48-7.41 (m, 2H), 7.40-7.33 (m, 2H), 7.31-7.25 (m, 3H), 2.90 (d, J = 5.8, 1H), 2.48 (d, J = 5.8, 1H), 1.46 (s, 3H), 1.01 (s, 3H). |
| | 2,2-Dimethyl-3-phenyl-cyclopropane-carboxylic acid (6-cyano-1H-benzoimidazol-2-yl)-amide | $^1$H NMR (400 MHz, DMSO/TFA) δ = 8.10 (dd, J = 1.4, 0.7, 1H), 7.85 (dd, J = 8.4, 0.7, 1H), 7.77 (dd, J = 8.4, 1.4, 1H), 7.46-7.09 (m, 5H), 2.94 (d, J = 5.8, 1H), 2.46 (d, J = 5.8, 1H), 1.46 (s, 3H), 1.03 (s, 3H). |
| | 2,2-Dimethyl-3-phenyl-cyclopropane-carboxylic acid (6-chloro-1H-benzoimidazol-2-yl)-amide | $^1$H NMR (400 MHz, DMSO/TFA) δ = 7.73 (dd, J = 1.4, 0.8, 1H), 7.70 (dd, J = 8.0, 0.8 m, 1H), 7.47 (dd, J = 8.0, 1.4, 1H), 7.39-7.33 (m, 2H), 7.32-7.24 (m, 3H), 2.88 (d, J = 5.8, 1H), 2.47 (d, J = 5.8, 1H), 1.46 (s, 3H), 1.00 (s, 3H). |
| | 2,2-Dimethyl-3-phenyl-cyclopropane-carboxylic acid (6-trifluoromethyl-1H-benzoimidazol-2-yl)-amide | $^1$H NMR (400 MHz, DMSO/TFA) δ = 8.01 (d, J = 1.2, 1H), 7.89 (d, J = 8.5, 1H), 7.74 (dd, J = 8.6, 1.2, 1H), 7.39-7.34 (m, 2H), 7.32-7.25 (m, 3H), 2.91 (d, J = 5.8, 1H), 2.49 (d, J = 5.8, 1H), 1.47 (s, 3H), 1.02 (s, 3H). |

2. Determination of Absolute Stereochemistry

The data shown in Table 1 for the pairs of trans-enantiomers strongly suggest that one enantiomer is significantly more active than the other. In order to determine which enantiomer is the more active one, attempts were made to determine the absolute stereochemistry of the enantiomers by means of single crystal x-ray crystallography.

In the case of 2-Phenyl-cyclopropanecarboxylic acid (6-bromo-3H-imidazo[4,5-b]pyridin-2-yl)-amide it was possible to obtain the absolute stereochemistry of the more active enantiomer which was found to be the S,S enantiomer (1S, 2S)-2-Phenyl-cyclopropanecarboxylic acid (6-bromo-3H-imidazo[4,5-b]pyridin-2-yl)-amide

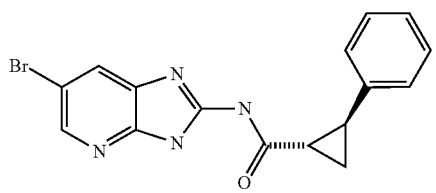

According to the classification used in Table 1 its IC$_{50}$ is "+++".

As in all pairs of enantiomers shown in Table 1 the less active enantiomer has an activity of only "+" or less, it is reasonable to assume that (1S,2S)-2-Phenyl-cyclopropanecarboxylic acid (6-bromo-3H-imidazo[4,5-b]pyridin-2-yl)- amide is in fact the more active enantiomer, and that, by way of analogy, the S,S enantiomer of all compounds according to the invention is the more active enantiomer.

The invention claimed is:

1. A method for treating cancer, comprising administering to a subject a compound of Formula (I)

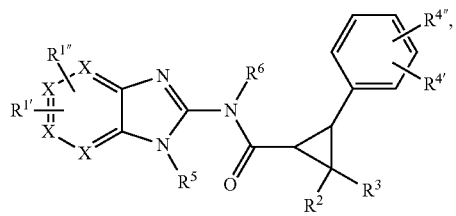
(I)

or its stereoisomers or tautomers, or pharmaceutically acceptable salts of each of the foregoing, including mixtures thereof in all ratios, wherein $R^{1'}$, $R^{1''}$, $R^{4'}$, $R^{4''}$ are each independently H, Hal, OH, CN, $NO_2$, $NH_2$, A, NH(LA), N(LA)$_2$, or COOH, $R^2$, $R^3$ are each independently H, LA or Hal, $R^5$, $R^6$ are each independently H or LA, X is C or N, wherein 0, 1 or 2 X are N, and the remaining X are C, A is a unbranched or branched alkyl based substituent having up to 15 carbon atoms, wherein one, two or three $CH_2$ groups may be replaced by O, S, NH, N(LA), CONH, NHCO, $SO_2$, COO or cyc, and 1-7H atoms may be replaced by Hal, and one $CH_3$ group may be replaced by cyc, LA is unbranched or branched alkyl having 1, 2, 3 or 4 carbon atoms, cyc is a mononuclear, aliphatic or aromatic, 4, 5 or 6 membered homo or heterocycle having 1 to 3 N—, O— and/or S atoms, and Hal is F, Cl, Br or I.

2. The method according to claim 1, wherein the compound is a compound of Formula (I'), or its stereoisomers or tautomers, or pharmaceutically acceptable salts of each of the foregoing, including mixtures thereof in all ratios, of

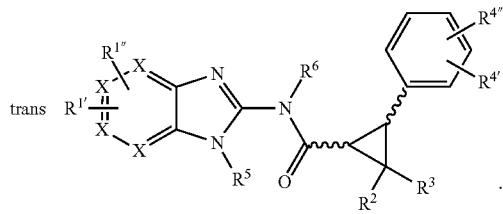
(I')

3. The method according to claim 1, or its stereoisomers or tautomers, or pharmaceutically acceptable salts of each of the foregoing, including mixtures thereof in all ratios, wherein the compound of formula (I) is a compound of any of Formulae (II''), (III''), (IV''), (V'') or (VI'')

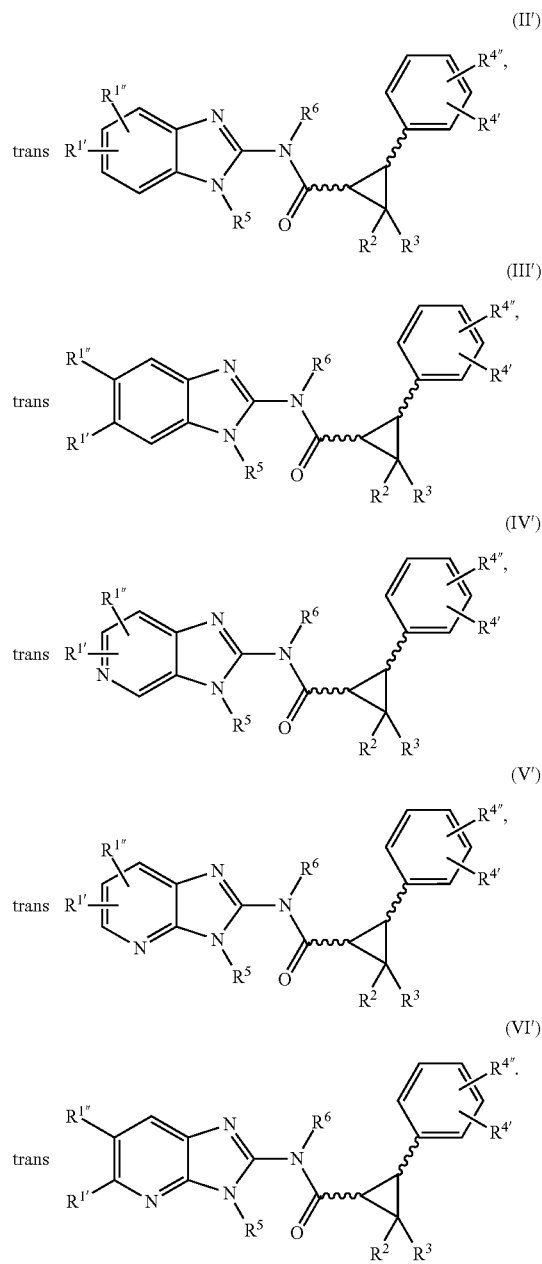

4. The method according to claim 1, wherein the compound is selected from the group consisting of:
2-m-Tolyl-cyclopropanecarboxylic acid (1H-benzoimidazol-2-yl)-amide,
2-Phenyl-cyclopropanecarboxylic acid (6-chloro-1H-benzoimidazol-2-yl)-amide,
2-(2-Chloro-phenyl)-cyclopropanecarboxylic acid (1H-benzoimidazol-2-yl)-amide,
2-Phenyl-cyclopropanecarboxylic acid (6-trifluoromethyl-1H-benzoimidazol-2-yl)-amide,
2-Phenyl-cyclopropanecarboxylic acid (5,6-dimethyl-1H-benzoimidazol-2-yl)-amide,
2-Phenyl-cyclopropanecarboxylic acid (5-methoxy-1H-benzoimidazol-2-yl)-amide,
2-Phenyl-cyclopropanecarboxylic acid (5-cyano-1H-benzoimidazol-2-yl)-amide, 2-(4-Fluoro-phenyl)-cyclopropanecarboxylic acid (1H-benzoimidazol-2-yl)-amide, 2-(3-Fluoro-phenyl)-cyclopropanecarboxylic acid (1H-benzoimidazol-2-yl)-amide, 2-(3-Nitro-phenyl)-cyclopropanecarboxylic acid (1H-benzoimidazol-2-yl)-amide, 2-(3-Bromo-phenyl)-cyclopropanecarboxylic acid (1H-benzoimidazol-2-yl)-amide, 2-(5-Bromo-2-fluoro-phenyl)-cyclopropanecarboxylic acid (1H-benzoimidazol-2-yl)-amide, 2-Phenyl-cyclopropanecarboxylic acid (5-ethyl-1H-benzoimidazol-2-yl)-amide, 2-Phenyl-cyclopropanecarboxylic acid (6-chloro-3H-imidazo[4,5-b]pyridin-2-yl)-amide, 2-Phenyl-cyclopropanecarboxylic acid (3H-imidazo[4,5-b]pyridin-2-yl)-amide, 2-Phenyl-cyclopropanecarboxylic acid (4-nitro-1H-benzoimidazol-2-yl)-amide, 2-(3-Fluoro-phenyl)-cyclopropanecarboxylic acid (6-chloro-3H-imidazo[4,5-b]pyridin-2-yl)-amide, 2-(2-Chloro-phenyl)-cyclopropanecarboxylic acid (1H-benzoimidazol-2-yl)-amide, 2-Phenyl-cyclopropanecarboxylic acid (4-amino-1H-benzoimidazol-2-yl)-amide, 2-Phenyl-cyclopropanecarboxylic acid (4-chloro-3H-imidazo[4,5-c]pyridin-2-yl)-amide, 2-Phenyl-cyclopropanecarboxylic acid (6-bromo-3H-imidazo[4,5-b]pyridin-2-yl)-amide, 2-(3-Fluoro-phenyl)-cyclopropanecarboxylic acid (6-cyano-1H-benzoimidazol-2-yl)-amide, 2-(2-Chloro-phenyl)-cyclopropanecarboxylic acid (6-trifluoromethyl-1H-benzoimidazol-2-yl)-amide, 2-Phenyl-cyclopropanecarboxylic acid (6-chloro-3H-imidazo[4,5-b]pyridin-2-yl)-amide, 2-Phenyl-cyclopropanecarboxylic acid (6-cyano-1H-benzoimidazol-2-yl)-amide, 2-Phenyl-cyclopropane-carboxylic acid (4-chloro-3H-imidazo[4,5-c]pyridin-2-yl)-amide, 2-Phenyl-cyclopropane-carboxylic acid (4-chloro-3H-imidazo[4,5-c]pyridin-2-yl)-amide, 2-(2-Chloro-phenyl)-cyclopropane-carboxylic acid (1H-benzoimidazol-2-yl)-amide, 2-(2-Chloro-phenyl)-cyclopropane-carboxylic acid (6-cyano-1H-benzoimidazol-2-yl)-amide, 2,2-Difluoro-3-phenyl-cyclopropane-carboxylic acid (6-chloro-1H-benzoimidazol-2-yl)-amide, 2-Phenyl-cyclopropanecarboxylic acid (1H-benzoimidazol-2-yl)-amide, wherein the compound has the trans configuration at the cyclopropyl ring, or its stereoisomers or tautomers, or pharmaceutically acceptable salts of each of the foregoing, including mixtures thereof in all ratios.

5. A pharmaceutical composition comprising a compound of Formula (I)

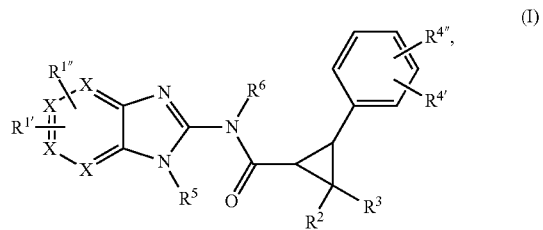

or its stereoisomers or tautomers, or pharmaceutically acceptable salts of each of the foregoing, including mixtures thereof in all ratios, wherein $R^{1'}$, $R^{1''}$, $R^{4'}$, $R^{4''}$ are each independently H, Hal, OH, CN, $NO_2$, $NH_2$, A, NH(LA), N(LA)$_2$, or COOH, $R^2$, $R^3$ are each independently H, LA or Hal, $R^5$, $R^6$ are each independently H or LA, X is C or N, wherein 0, 1 or 2 X are N, and the remaining X are C, A is a unbranched or branched alkyl based substituent having up to 15 carbon atoms, wherein one, two or three $CH_2$ groups may be replaced by O, S, NH, N(LA), CONH, NHCO, $SO_2$, COO or cyc, and 1-7H atoms may be replaced by Hal, and one $CH_3$ group may be replaced by cyc, LA is unbranched or branched alkyl having 1, 2, 3 or 4 carbon atoms, cyc is a mononuclear, aliphatic or aromatic, 4, 5 or 6 membered homo or heterocycle having 1 to 3 N—, O— and/or S atoms, and Hal is F, Cl, Br or I, together with a pharmaceutically acceptable carrier.

6. A kit consisting of separate packs of a) an effective amount of a compound of Formula (I)

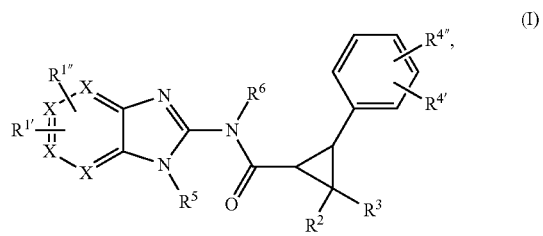

or its stereoisomers or tautomers, or pharmaceutically acceptable salts of each of the foregoing, including mixtures thereof in all ratios, wherein $R^{1'}$, $R^{1''}$, $R^{4'}$, $R^{4''}$ are each independently H, Hal, OH, CN, $NO_2$, $NH_2$, A, NH(LA), N(LA)$_2$, or COOH, $R^2$, $R^3$ are each independently H, LA or Hal, $R^5$, $R^6$ are each independently H or LA, X is C or N, wherein 0, 1 or 2 X are N, and the remaining X are C, A is a unbranched or branched alkyl based substituent having up to 15 carbon atoms, wherein one, two or three $CH_2$ groups may be replaced by O, S, NH, N(LA), CONH, NHCO, $SO_2$, COO or cyc, and 1-7H atoms may be replaced by Hal, and one $CH_3$ group may be replaced by cyc, LA is unbranched or branched alkyl having 1, 2, 3 or 4 carbon atoms,
cyc is a mononuclear, aliphatic or aromatic, 4, 5 or 6 membered homo or heterocycle having 1 to 3 N—, O— and/or S atoms, and
Hal is F, Cl, Br or I and
b) an effective amount of a further medicament active ingredient.

7. A compound of Formula (I)

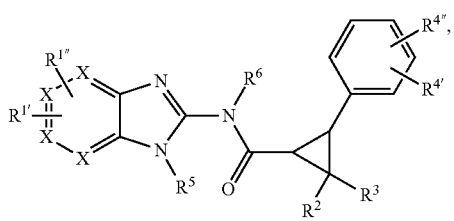
(I)

or its stereoisomers or tautomers, or pharmaceutically acceptable salts of each of the foregoing, including mixtures thereof in all ratios, wherein
$R^{1'}$, $R^{1''}$, $R^{4'}$, $R^{4''}$ are each independently H, Hal, OH, CN, $NO_2$, $NH_2$, A, NH(LA), N(LA)$_2$, or COOH,
$R^2$, $R^3$ are each independently H, LA or Hal,
$R^5$, $R^6$ are each independently H or LA,
X is C or N, wherein 0, 1 or 2 X are N, and the remaining X are C,
A is a unbranched or branched alkyl based substituent having up to 15 carbon atoms, wherein one, two or three $CH_2$ groups may be replaced by O, S, NH, N(LA), CONH, NHCO, $SO_2$, COO or cyc, and 1-7H atoms may be replaced by Hal, and one $CH_3$ group may be replaced by cyc,
LA is unbranched or branched alkyl having 1, 2, 3 or 4 carbon atoms,
cyc is a mononuclear, aliphatic or aromatic, 4, 5 or 6 membered homo or heterocycle having 1 to 3 N—, O— and/or S atoms, and
Hal is F, Cl, Br or I,
with the proviso that said compound is not
2-Phenyl-cyclopropanecarboxylic acid (6-methanesulfonyl-benzothiazol-2-yl)-amide,
Phenyl-cyclopropanecarboxylic acid (1H-benzoimidazol-2-yl)-amide,
N-[1-[2-(diethylamino)ethyl]-1H-benzimidazol-2-yl]-2-phenyl-cyclopropane carboxamide,
N-(1-methyl-1H-benzimidazol-2-yl)-2-phenyl-cyclopropane carboxamide,
2-phenyl-N-(1-propyl-1H-benzimidazol-2-yl-cyclopropane carboxamide,
N-(1-ethyl-1H-benzimidazol-2-yl)-2-phenyl-cyclopropane carboxamide,
2-(4-chlorophenyl)-N-(1-methyl-1H-benzimidazol-2-yl)-cyclopropane carboxamide, or
N-1H-benzimidazol-2-yl-2-phenyl-cyclopropane carboxamide.

8. The compound according to claim 7, or its stereoisomers or tautomers, or pharmaceutically acceptable salts of each of the foregoing, including mixtures thereof in all ratios, of Formula (I')

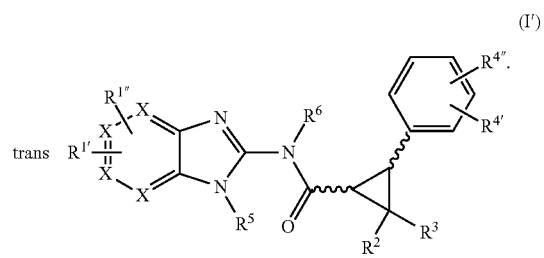
(I')

9. The compound according to claim 8, or its stereoisomers or tautomers, or pharmaceutically acceptable salts of each of the foregoing, including mixtures thereof in all ratios, of any of Formulae (II'), (III'), (IV'), (V') or (VI')

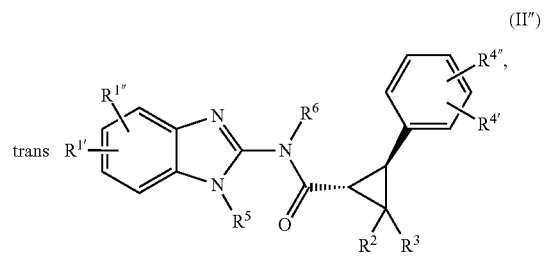
(II'')

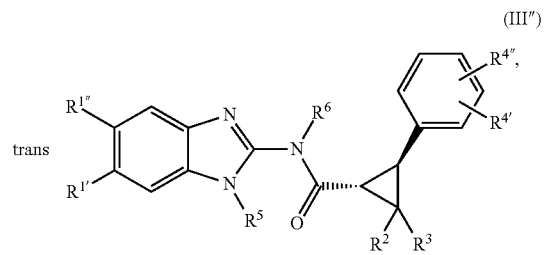
(III'')

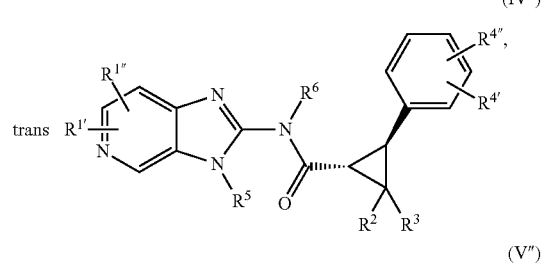
(IV'')

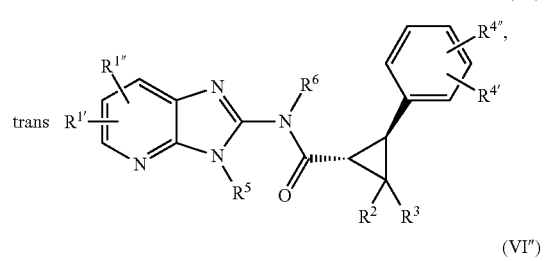
(V'')

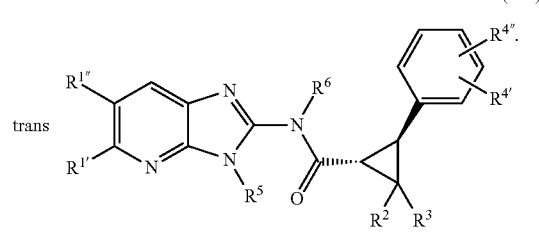
(VI'')

10. The compound according to claim 9, or its stereoisomers or tautomers, or pharmaceutically acceptable salts of each of the foregoing, including mixtures thereof in all ratios, of Formula (I″)

(I″)
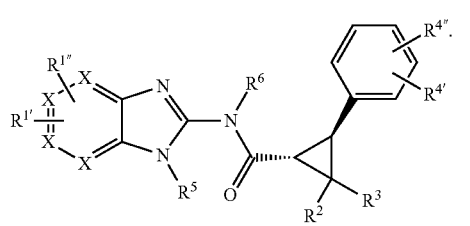

11. The compound according to claim 10, or its stereoisomers or tautomers, or pharmaceutically acceptable salts of each of the foregoing, including mixtures thereof in all ratios, of any of Formulae (II″), (III″), (IV″), (V″) or (VI″)

(II″)
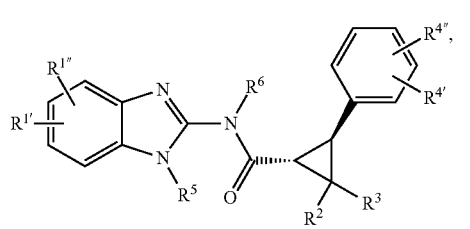

(III″)
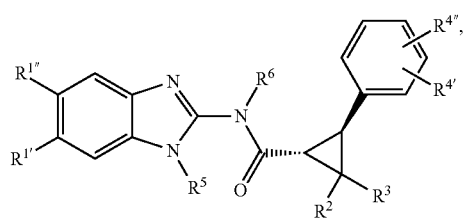

(IV″)
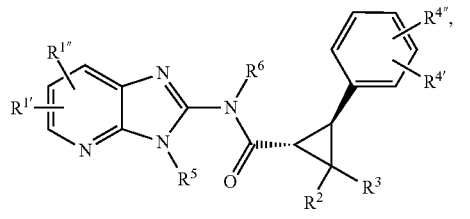

(V″)
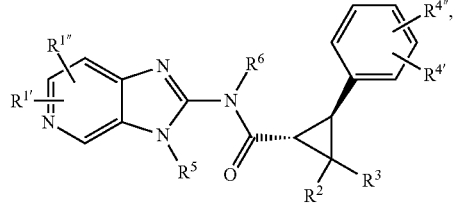

(VI″)
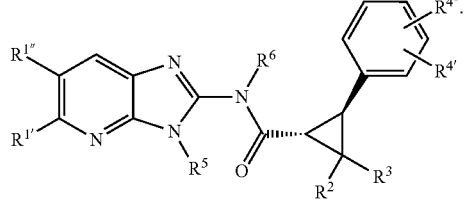

12. The compound according to claim 7, or its stereoisomers or tautomers, or pharmaceutically acceptable salts of each of the foregoing, including mixtures thereof in all ratios, wherein $R^{1'}$, $R^{1'''}$ are each independently H, F, Cl, Br, CN, $NO_2$, methyl or ethyl.

13. The compound according to claim 7, wherein the compound is selected from the group consisting of:

2-m-Tolyl-cyclopropanecarboxylic acid (1H-benzoimidazol-2-yl)-amide,

2-Phenyl-cyclopropanecarboxylic acid (6-chloro-1H-benzoimidazol-2-yl)-amide, 2-(2-Chloro-phenyl)-cyclopropanecarboxylic acid (1H-benzoimidazol-2-yl)-amide, 2-Phenyl-cyclopropanecarboxylic acid (6-trifluoromethyl-1H-benzoimidazol-2-yl)-amide, 2-Phenyl-cyclopropanecarboxylic acid (5,6-dimethyl-1H-benzoimidazol-2-yl)-amide, 2-Phenyl-cyclopropanecarboxylic acid (5-methoxy-1H-benzoimidazol-2-yl)-amide, 2-Phenyl-cyclopropanecarboxylic acid (5-cyano-1H-benzoimidazol-2-yl)-amide, 2-(4-Fluoro-phenyl)-cyclopropanecarboxylic acid (1H-benzoimidazol-2-yl)-amide, 2-(3-Fluoro-phenyl)-cyclopropanecarboxylic acid (1H-benzoimidazol-2-yl)-amide, 2-(3-Nitro-phenyl)-cyclopropanecarboxylic acid (1H-benzoimidazol-2-yl)-amide, 2-(3-Bromo-phenyl)-cyclopropanecarboxylic acid (1H-benzoimidazol-2-yl)-amide, 2-(5-Bromo-2-fluoro-phenyl)-cyclopropanecarboxylic acid (1H-benzoimidazol-2-yl)-amide, 2-Phenyl-cyclopropanecarboxylic acid (5-ethyl-1H-benzoimidazol-2-yl)-amide, 2-Phenyl-cyclopropanecarboxylic acid (6-chloro-3H-imidazo[4,5-b]pyridin-2-yl)-amide, 2-Phenyl-cyclopropanecarboxylic acid (3H-imidazo[4,5-b]pyridin-2-yl)-amide, 2-Phenyl-cyclopropanecarboxylic acid (4-nitro-1H-benzoimidazol-2-yl)-amide, 2-(3-Fluoro-phenyl)-cyclopropanecarboxylic acid (6-chloro-3H-imidazo[4,5-b]pyridin-2-yl)-amide, 2-(2-Chloro-phenyl)-cyclopropanecarboxylic acid (1H-benzoimidazol-2-yl)-amide, 2-Phenyl-cyclopropanecarboxylic acid (4-amino-1H-benzoimidazol-2-yl)-amide, 2-Phenyl-cyclopropanecarboxylic acid (4-chloro-3H-imidazo[4,5-c]pyridin-2-yl)-amide, 2-Phenyl-cyclopropanecarboxylic acid (6-bromo-3H-imidazo[4,5-b]pyridin-2-yl)-amide, 2-(3-Fluoro-phenyl)-cyclopropanecarboxylic acid (6-cyano-1H-benzoimidazol-2-yl)-amide, 2-(2-Chloro-phenyl)-cyclopropanecarboxylic acid (6-trifluoromethyl-1H-benzoimidazol-2-yl)-amide, 2-Phenyl-cyclopropanecarboxylic acid (6-chloro-3H-imidazo[4,5-b]pyridin-2-yl)-amide, 2-Phenyl-cyclopropanecarboxylic acid (6-cyano-1H-benzoimidazol-2-yl)-amide, 2-Phenyl-cyclopropane-carboxylic acid (4-chloro-3H-imidazo[4,5-c]pyridin-2-yl)-amide,
2-Phenyl-cyclopropane-carboxylic acid (4-chloro-3H-imidazo[4,5-c]pyridin-2-yl)-amide,
2-(2-Chloro-phenyl)-cyclopropane-carboxylic acid (1H-benzoimidazol-2-yl)-amide,
2-(2-Chloro-phenyl)-cyclopropane-carboxylic acid (6-cyano-1H-benzoimidazol-2-yl)-amide,
2,2-Difluoro-3-phenyl-cyclopropane-carboxylic acid (6-chloro-1H-benzoimidazol-2-yl)-amide,
wherein the compound has the trans configuration at the cyclopropyl ring, or its stereoisomers or tautomers, or pharmaceutically acceptable salts of each of the foregoing, including mixtures thereof in all ratios.

14. Process for the manufacture of compounds of Formula (I), wherein a compound of Formula (VIII)

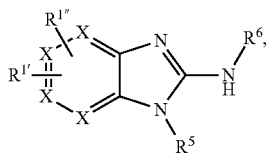

is reacted with a compound of Formula (VII)

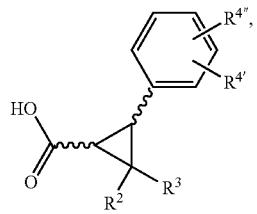

to yield a compound of Formula (I).

15. The compound according to claim 7, wherein $R^{1'}$ is H, and $R^{1'''}$ is F, Cl, Br, CN, $NO_2$, methyl or ethyl.

16. The compound according to claim 7, wherein $R^{4'}$ and $R^{4''}$ are each independently H, F, Cl or Br.

17. The compound according to claim 7, wherein $R^2$ and $R^3$ are each independently H or F.

18. The compound according to claim 7, wherein $R^{1'}$ is CN and $R^{1'''}$ is H.

19. The compound according to claim 7, wherein $R^{1'}$ and $R^{1'}$ are each H.

* * * * *